United States Patent
Araki

(10) Patent No.: US 7,632,615 B2
(45) Date of Patent: Dec. 15, 2009

(54) COLORANT-CONTAINING CURABLE COMPOSITION, COLOR FILTER USING THE COMPOSITION, AND METHOD FOR MANUFACTURING THE SAME

(75) Inventor: Katsumi Araki, Shizuoka-ken (JP)

(73) Assignee: FUJIFILM Corporation, Tokyo (JP)

( * ) Notice: Subject to any disclaimer, the term of this patent is extended or adjusted under 35 U.S.C. 154(b) by 330 days.

(21) Appl. No.: 11/778,172

(22) Filed: Jul. 16, 2007

(65) Prior Publication Data
US 2008/0014536 A1 Jan. 17, 2008

Related U.S. Application Data

(62) Division of application No. 11/095,515, filed on Apr. 1, 2005, now Pat. No. 7,276,548.

(30) Foreign Application Priority Data

Apr. 20, 2004 (JP) ............................. 2004-110469
May 17, 2004 (JP) ............................. 2004-146659

(51) Int. Cl.
*G02B 5/20* (2006.01)
*G03F 7/00* (2006.01)

(52) U.S. Cl. ........................................................ 430/7

(58) Field of Classification Search ........................ None
See application file for complete search history.

(56) References Cited

U.S. PATENT DOCUMENTS

| 6,248,482 B1* | 6/2001 | Kashiwazaki et al. .......... 430/7 |
| 2002/0034697 A1* | 3/2002 | Machiguchi et al. ........... 430/7 |
| 2002/0045111 A1* | 4/2002 | Machiguchi et al. ........... 430/7 |

FOREIGN PATENT DOCUMENTS

| JP | 2-199403 A | 8/1990 |
| JP | 4-76062 A | 3/1992 |
| JP | 5-273411 A | 10/1993 |
| JP | 6-184482 A | 7/1994 |
| JP | 7-140654 A | 6/1995 |
| JP | 2002-278056 A | 9/2002 |

* cited by examiner

*Primary Examiner*—John A. McPherson
(74) *Attorney, Agent, or Firm*—Sughrue Mion, PLLC

(57) ABSTRACT

The present invention provides a colorant-containing curable composition comprising a colorant, wherein the colorant contains a compound represented by the following Formula (I).

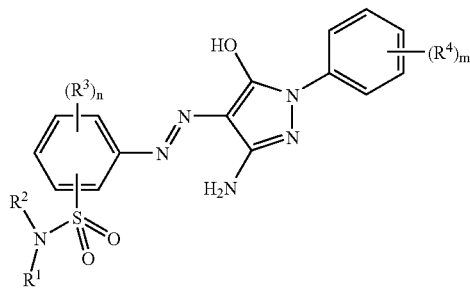

Formula (I)

In Formula (I), $R^1$ and $R^2$ each independently represent H, an alkyl group, an alkenyl group, an aryl group, or an aralkyl group. $R^1$ and $R^2$ may be formed into a heterocycle together with a jointly bonded nitrogen atom. $R^3$ represents a halogen atom, a trihalomethyl group, an alkoxy group, a nitro group, or an amino group. n represents an integer of 0 to 4. $R^4$ represents a halogen atom or a $—SO_3M$ group, in which M represents H, a cation of a metallic atom, or a cation consisting of a nitrogen-containing compound. m represents an integer of 0 to 5. The present invention further provides a color filter comprising the compound represented by Formula (I) and a method for manufacturing the color filter.

3 Claims, No Drawings

COLORANT-CONTAINING CURABLE COMPOSITION, COLOR FILTER USING THE COMPOSITION, AND METHOD FOR MANUFACTURING THE SAME

CROSS-REFERENCE TO RELATED APPLICATION

This is a Divisional application of U.S. Ser. No. 11/095,515 filed Apr. 1, 2005, now U.S. Pat. No. 7,276,548, which claims priority under 35 U.S.C. 119 from Japanese Patent Application Nos. 2004-110469 and 2004-146659, the disclosures of which are incorporated by reference herein.

BACKGROUND OF THE INVENTION

1. Field of the Invention

The present invention relates to a colorant-containing curable composition for a color filter that is suitable for forming a colored image of a color filter for use with a liquid crystal display device, a solid image pickup element (such as a CCD or a CMOS) and the like, a color filter, and a method for manufacturing the same.

2. Description of the Related Art

As methods for manufacturing a color filter for use with a liquid crystal display device or a solid image pickup element, dyeing methods, printing methods, electrodeposition methods, and pigment dispersion methods are known.

Among these, the pigment dispersion method is a method for manufacturing a color filter by a photolithography method including using a colored radiation-sensitive composition in which pigments are dispersed in various photosensitive compositions. The pigment dispersion method has an advantage of stability against light, heat and the like, because of the use of pigments. In addition, because the pigment dispersion method conducts patterning by the photolithography method, it gives high positioning accuracy. Therefore, the pigment dispersion method has been widely used as a method which is suitable for manufacturing color filters for color displays of large-screens and high-precision.

In order to manufacture a color filter by the pigment dispersion method: a radiation-sensitive composition is coated on a glass substrate by means of a spin coater, a roll coater, or the like, and dried to form a coating film; the coating film is exposed to light through a mask pattern, and developed to form colored pixels; and this cycle of operation is repeated for each color.

A negative photosensitive composition, which uses a photopolymerizable monomer and a photopolymerization initiator in an alkali soluble resin, is conventionally known as a specific example of the sensitive compositions used in the pigment dispersion method (see, for example, Japanese Patent Application Laid-Open (JP-A) Nos. 2-199403, 4-76062, 5-273411, 6-184482, and 7-140654).

In recent years, for applications such as solid image pickup elements, higher precision of the color filter has been demanded. However, it is difficult to further improve the resolution with the conventional pigment dispersion system. In addition, there are problems, such as irregular color being caused by coarse particles of the pigment. Therefore, the above-mentioned pigment dispersion method has not been suited for applications such as solid image pickup elements where extremely fine patterns are required.

In order to solve the above-mentioned problems, examples where a solvent or water soluble dye is used have been conventionally known (see, for example, Japanese Patent Application Laid-Open (JP-A) No. 2002-278056).

However, the dye-containing curable composition has the following problems (1) to (4).

(1) Generally, coloring matter has a low solubility in either alkali water solutions or organic solvents, thus it is difficult to obtain a liquid curing composition having the desired spectrum.

(2) Dyes often interact with other components in the curable composition, thus it is difficult to adjust the solubility of the curing part and the non-curing part (developability).

(3) When the dye has a low molar absorption coefficient ($\epsilon$), the dye must be added in a large quantity, thus it is inevitable that the amounts of the other components in the curable composition, such as the polymerizable compound (monomer), the binder, and the photopolymerization initiator, must be reduced. This presents such problems as the lowering of the curability of the composition, the heat resistance after curing, and the developability of the (non-)curing part.

(4) Dyes are generally inferior in light resistance and heat resistance, as compared to pigments.

In addition, especially for the application for manufacturing of a color filter for a solid image pickup element, it is required that the film thickness be 1.5 µm or less, unlike in semiconductor manufacturing applications. Therefore, the coloring matter must be added to the curable composition in a large quantity, which presents the same problems as mentioned above.

Because of the above-mentioned problems, it has been difficult in practice to meet the requirements for performance for use in extremely fine, thin-film colored patterns for high-precision color filters. Therefore, development of a dye and curable composition which can eliminate the above-mentioned problems has been desired.

SUMMARY OF THE INVENTION

The present invention has been made in view of the above circumstances and provides a colorant-containing curable composition which has: a high sensitivity, a high resolution, a high heat resistance, and a wide development latitude; yet is free from elution of the dye; is excellent in solvent resistance of the pattern; and with high productivity. Also provided is a color filter using the same, and the manufacturing method of the same.

Particularly, the present invention provides a colorant-containing curable composition which is excellent in molar absorbance coefficient and color value of the dye, light resistance, heat resistance, and pattern formability (developability), as well as a color filter using the same, and the manufacturing method of the same.

According to the present invention, a colorant-containing curable composition for a color filter containing the following compound with a specific structure having an aminopyrazolone skeleton together with a sulfonamide group is provided to achieve the purpose of the present invention.

Namely, the present invention provides a colorant-containing curable composition comprising a colorant, wherein the colorant contains a compound represented by the following Formula (I).

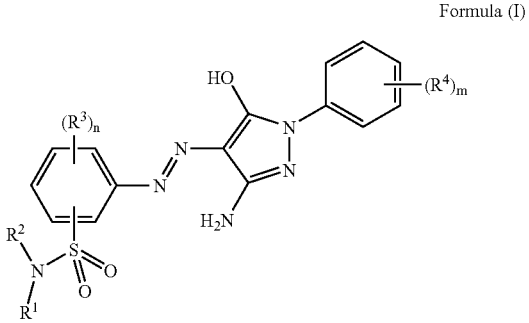

Formula (I)

In Formula (I), $R^1$ and $R^2$ each independently represent a hydrogen atom, an alkyl group having 1 to 21 carbon atoms, an alkenyl group having 2 to 21 carbon atoms, an aryl group having 6 to 21 carbon atoms, or an aralkyl group having 7 to 21 carbon atoms. $R^1$ and $R^2$ may be formed into a heterocycle together with a jointly bonded nitrogen atom. $R^3$ represents a halogen atom, a trihalomethyl group, an alkoxy group having 1 to 21 carbon atoms, a nitro group, or an amino group. n represents an integer of 0 to 4. $R^4$ represents a halogen atom or a —$SO_3M$ group, in which M represents a hydrogen atom, a cation of a metallic atom, or a cation consisting of a nitrogen-containing compound. m represents an integer of 0 to 5.

The present invention further provides a color filter comprising the compound represented by Formula (I).

The present invention further provides a method for manufacturing the color filter, comprising coating a colorant-containing curable composition on a support, exposing the resultant to light through a mask, and developing the resultant to form a pattern, wherein the colorant-containing curable composition at least contains a colorant, and the colorant contains the compound represented by Formula (I).

DETAILED DESCRIPTION OF THE INVENTION

Hereinafter, the colorant-containing curable composition of the present invention, the color filter, and the manufacturing method thereof will be described in detail.

Colorant-Containing Curable Composition

The colorant-containing curable composition of the present invention (which, hereinafter, may sometimes be referred to as "the composition of the present invention") is a colorant-containing curable composition which contains at least a colorant, wherein said colorant contains a compound which is represented by the following Formula (I):

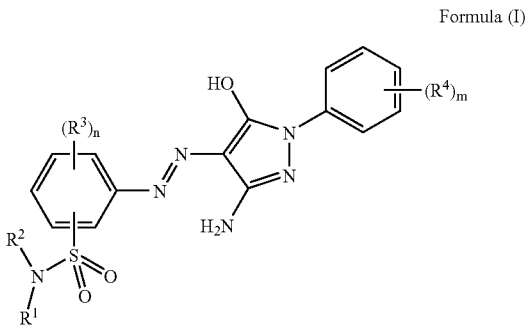

Formula (I)

In Formula (I), $R^1$ and $R^2$ each independently represent a hydrogen atom, an alkyl group having 1 to 21 carbon atoms, an alkenyl group having 2 to 21 carbon atoms, an aryl group having 6 to 21 carbon atoms, or an aralkyl group having 7 to 21 carbon atoms. $R^1$ and $R^2$ may be formed into a heterocycle together with a jointly bonded nitrogen atom. $R^3$ represents a halogen atom, a trihalomethyl group, an alkoxy group having 1 to 21 carbon atoms, a nitro group, or an amino group. n represents an integer of 0 to 4. $R^4$ represents a halogen atom, or an —$SO_3M$ group, in which M represents a hydrogen atom, a cation of a metallic atom, or a cation consisting of a nitrogen-containing compound. m represents an integer of 0 to 5.

By containing a compound which is represented by Formula (I), the composition of the present invention is capable of showing excellent performance in heat resistance, light resistance, and molar absorption coefficient (color value) of the colorant.

In addition, because the composition of the present invention has been improved especially in color value, the amount of addition of the dye can be reduced. Thereby, the contents of the other additives can be increased, and thus the various performances of the resist can be improved. Further, according to the composition of the present invention, the developability of the unexposed areas and the percentage of film remaining for the exposed areas can be improved, thus a good pattern formability can be provided. In addition, the composition of the present invention provides high productivity, because there is no possibility of degradation of the various above-mentioned performances in the manufacturing process.

The composition of the present invention contains at least a colorant, and this is generally used with a solvent. In addition, when required, it may contain a binder, a polymerizable compound, a photopolymerization initiator, a crosslinking agent, a photo sensitizer, a photo-acid generator, or the like.

Specifically, when the composition of the present invention is of negative composition, it may contain a solvent, a polymerizable compound (monomer), a binder (preferably, an alkali soluble binder) and a photopolymerization initiator in addition to the above-mentioned colorant, and further may contain a crosslinking agent.

When the composition of the present invention is a positive composition, it contains an organic solvent or curing agent, and a photo sensitizer or a photo-acid generator, in addition to the above-mentioned colorant.

The composition of the present invention contains a compound represented by Formula (I) as a colorant. The composition of the present invention may contain two or more different compounds represented by Formula (I). Hereinafter, the colorant (coloring matter compound) in the present invention will be described in detail.

The compound represented by the above-mentioned Formula (I) is a compound which simultaneously meets the requirements for high light resistance and high heat resistance (not conventionally possible), and is capable of being freely dissolved in water or a solvent as needed.

In Formula (I), $R^1$ and $R^2$ each independently represent a hydrogen atom, an alkyl group having 1 to 21 carbon atoms, an alkenyl group having 2 to 21 carbon atoms, an aryl group having 6 to 21 carbon atoms, or an aralkyl group having 7 to 21 carbon atoms. $R^1$ and $R^2$ may be formed into a heterocycle together with a jointly bonded nitrogen atom.

In Formula (I), the alkyl group having 1 to 21 carbon atoms that is represented by $R^1$ and $R^2$ may have a substituent. In addition, the alkyl group having 1 to 21 carbon atoms may be a straight-chain or branched group, or otherwise a cyclic alkyl group.

Preferable examples of the alkyl group include a methyl group, an ethyl group, an n-propyl group, an n-butyl group, an n-amyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-eicosanyl group, an i-propyl group, a sec-butyl group, an i-butyl group, a t-butyl group, a 1-methylbutyl group, a 1-ethylpropyl group, a 2-methylbutyl group, an i-amyl group, a neopentyl group, a 1,2-dimethylpropyl group, a 1,1-dimethylpropyl group, a t-amyl group, a 1,3-dimethylbutyl group, a 3,3-dimethylbutyl group, a 2-ethylbutyl group, a 2-ethyl-2-methylpropyl group, a straight-chain or branched heptyl group, a 1-methylheptyl group, a 2-ethylhexyl group, a 1,5-dimethylhexyl group, a t-octyl group, a branched nonyl group, a branched decyl group, a branched undecyl group, a branched dodecyl group, a branched tridecyl group, a branched tetradecyl group, a branched pentadecyl group, a branched hexadecyl group, a branched heptadecyl group, a branched octadecyl group, a straight-chain or branched nonadecyl group, a straight-chain or branched eicosanyl group, a cyclopropyl group, a cyclopropylmethyl group, a cyclobutyl group, a cyclobutylmethyl group, a cyclopentyl group, a cyclohexyl group, a cyclohexylmethyl group, a cycloheptyl group, a cyclooctyl group, a cyclohexylpropyl group, a cyclododecyl group, a norbornyl group, a bornyl group, a cys-myrtanyl group, an isopinocamphenyl group, a noradamantyl group, an adamantyl group, an adamantylmethyl group, a 1-(1-adamantyl)ethyl group, a 3,5-dimethyladamantyl group, a quinuclidinyl group, a cyclopentylethyl group, and a bicyclooctyl group.

Among these, the methyl group, the ethyl group, the n-propyl group, the n-butyl group, the n-amyl group, the n-hexyl group, the n-heptyl group, the n-octyl group, the n-nonyl group, the n-decyl group, the n-undecyl group, the n-dodecyl group, the n-tridecyl group, the n-tetradecyl group, the i-propyl group, the sec-butyl group, the i-butyl group, the t-butyl group, the 1-methylbutyl group, the 1-ethylpropyl group, the 2-methylbutyl group, the i-amyl group, the neopentyl group, the 1,2-dimethylpropyl group, the 1,1-dimethylpropyl group, the t-amyl group, the 1,3-dimethylbutyl group, the 3,3-dimethylbutyl group, the 2-ethylbutyl group, the 2-ethyl-2-methylpropyl group, the straight-chain or branched heptyl group, the 1-methylheptyl group, the 2-ethylhexyl group, the 1,5-dimethylhexyl group, the t-octyl group, the branched nonyl group, the branched decyl group, the branched undecyl group, the branched dodecyl group, the branched tridecyl group, the branched tetradecyl group, the cyclopropyl group, the cyclopropylmethyl group, the cyclobutyl group, the cyclobutylmethyl group, the cyclopentyl group, the cyclohexyl group, the cyclohexylmethyl group, the cycloheptyl group, the cyclooctyl group, the cyclohexylpropyl group, the cyclododecyl group, the norbornyl group, the bornyl group, the cys-myrtanyl group, the isopinocamphenyl group, the noradamantyl group, the adamantyl group, the adamantylmethyl group, the 1-(1-adamantyl)ethyl group, the 3,5-dimethyladamantyl group, the quinuclidinyl group, the cyclopentylethyl group, and the bicyclooctyl group are more preferable, and further the methyl group, the ethyl group, the n-propyl group, the n-butyl group, the n-amyl group, the n-hexyl group, the n-heptyl group, the n-octyl group, the n-nonyl group, the n-decyl group, the i-propyl group, the sec-butyl group, the i-butyl group, the t-butyl group, the 1-methylbutyl group, the 1-ethylpropyl group, the 2-methylbutyl group, the i-amyl group, the neopentyl group, the 1,2-dimethylpropyl group, the 1,1-dimethylpropyl group, the t-amyl group, the 1,3-dimethylbutyl group, the 3,3-dimethylbutyl group, the 2-ethylbutyl group, the 2-ethyl-2-methylpropyl group, the straight-chain or branched heptyl group, the 1-methylheptyl group, the 2-ethylhexyl group, the 1,5-dimethylhexyl group, the t-octyl group, the branched nonyl group, the branched decyl group, the cyclopropyl group, the cyclopropylmethyl group, the cyclobutyl group, the cyclobutylmethyl group, the cyclopentyl group, the cyclohexyl group, the cyclohexylmethyl group, the cycloheptyl group, the cyclooctyl group, the cyclohexylpropyl group, the cyclododecyl group, the norbornyl group, the bornyl group, the noradamantyl group, the adamantyl group, the adamantylmethyl group, the 1-(1-adamantyl)ethyl group, the 3,5-dimethyladamantyl group, the cyclopentylethyl group, and the bicyclooctyl group are particularly preferable.

Among the above-mentioned alkyl groups, in view of improvement in heat resistance, the ethyl group, the n-propyl group, the n-butyl group, the n-amyl group, the n-hexyl group, the n-heptyl group, the n-octyl group, the n-nonyl group, the n-decyl group, the i-propyl group, the sec-butyl group, the i-butyl group, the t-butyl group, the 1-methylbutyl group, the 1-ethylpropyl group, the 2-methylbutyl group, the i-amyl group, the neopentyl group, the 1,2-dimethylpropyl group, the 1,1-dimethylpropyl group, the t-amyl group, the 1,3-dimethylbutyl group, the 3,3-dimethylbutyl group, the 2-ethylbutyl group, the 2-ethyl-2-methylpropyl group, the branched heptyl group, the 1-methylheptyl group, the 1,5-dimethylhexyl group, the t-octyl group, the branched nonyl group, the branched decyl group, the cyclopropyl group, the cyclopropylmethyl group, the cyclobutyl group, the cyclobutylmethyl group, the cyclopentyl group, the cyclohexyl group, the cyclohexylmethyl group, the cycloheptyl group, the cyclooctyl group, the cyclohexylpropyl group, the cyclododecyl group, the norbornyl group, the bornyl group, the noradamantyl group, the adamantyl group, the adamantylmethyl group, the 1-(1-adamantyl)ethyl group, the 3,5-dimethyladamantyl group, the cyclopentylethyl group, and other branched alkyl groups and cyclic alkyl groups are particularly preferable.

As the alkyl group represented by $R^1$ and $R^2$ in Formula (I), an alkyl group which is specifically substituted by fluorine may be used. Specific preferable examples of the alkyl group include a trifluoromethyl group, a trifluoroethyl group, a pentafluoroethyl group, a heptafluoropropyl group, a nonafluorobutyl group, a tridecafluorohexyl group, a pentadecafluoroheptyl group, a heptadecafluorooctyl group, a tridecafluorooctyl group, a nonafluorononyl group, a heptadecafluorodecyl group, and a perfluorodecyl group are preferable; among these, the trifluoromethyl group, the pentafluoroethyl group, the heptafluoropropyl group, the nonafluorobutyl group, the tridecafluorohexyl group, and the pentadecafluoroheptyl group are more preferable; and the trifluoromethyl group, the pentafluoroethyl group, the heptafluoropropyl group, the nonafluorobutyl group, and the tridecafluorohexyl group.

In Formula (I), the alkenyl group that has 2 to 21 carbon atoms and that is represented by $R^1$ and $R^2$ may have a substituent. Preferable examples of the alkenyl group having 2 to 21 carbon atoms and that is represented by $R^1$ and $R^2$ include a vinyl group, an isopropenyl group, a 2-propenyl group, a 2-methyl-propenyl group, a 1-methyl-1-propenyl group, a 1-butenyl group, a 3-butenyl group, a 1-methyl-1-butenyl group, a 1,1-dimethyl-3-butenyl group, a 1-pentenyl group, a 2-pentenyl group, a 1-ethyl-1-pentenyl group, a 1-hexenyl group, a 1-heptenyl group, a 2,6-dimethyl-5-heptenyl group, a 9-decenyl group, a 1-cyclopentenyl group, a 2-cyclopentenylmethyl group, a cyclohexenyl group, a 1-methyl-2-cyclohexenyl group, a 1,4-dihydro-2-methylphenyl group, an octenyl group, a citroneryl group, an oleyl group, a gelanyl group, a farnecyl group, and a 2-(1-cyclohexenyl)ethyl group; among these, the vinyl group, the isopropenyl group, the 2-propenyl group, the 2-methyl-propenyl group, the 1-methyl-1-propenyl group, the 1-butenyl group, the 3-butenyl group, the 1-methyl-1-butenyl group, the 1,1-dimethyl-3-butenyl group, the 1-pentenyl group, the 2-pentenyl group, the 1-ethyl-1-pentenyl group, the 1-hexenyl group, the 1-heptenyl group, the 1-cyclopentenyl group, the 2-cyclopentenyl-methyl group, the cyclohexenyl group, the 1-methyl-2-cyclohexenyl group, and the 1,4-dihydro-2-methylphenyl group are more preferable; and further, the vinyl group, the isopropenyl group, the 2-propenyl group, the 2-methyl-propenyl group, the 1-methyl-1-propenyl group, the 1-butenyl group, the 3-butenyl group, the 1-methyl-1-butenyl group, the 1,1-dimethyl-3-butenyl group, the 1-pentenyl group, the 2-pentenyl group, the 1-ethyl-1-pentenyl group, the 1-hexenyl group, the 1-cyclopentenyl group, the 2-cyclopentenylmethyl group, the cyclohexenyl group, the 1-methyl-2-cyclohexenyl group, and the 1,4-dihydro-2-methylphenyl group are particularly preferable.

The aryl group that has 6 to 21 carbon atoms and that is represented by $R^1$ and $R^2$ may have a substituent. Preferable examples of the aryl group that has 6 to 21 carbon atoms and that may have a substituent include a phenyl group, a naphthyl group, biphenylenyl group, an acenaphtenyl group, a fluolenyl group, an anthracenyl group, an anthraquinonyl group, a pirenyl group, and the like; among these, the phenyl group, the naphthyl group, the biphenylenyl group, the acenaphtenyl group, the fluolenyl group, the anthracenyl group, and the like are more preferable; and further, the phenyl group, the naphthyl group, the biphenylenyl group, the fluolenyl group, and the like are particularly preferable.

The aralkyl group that has 7 to 21 carbon atoms and that is represented by $R^1$ and $R^2$ may have a substituent.

Preferable examples of the aralkyl group that has 7 to 21 carbon atoms and that may have a substituent include a benzyl group, a diphenylmethyl group, a 1,2-diphenylethyl group, a phenyl-cyclopentylmethyl group, an α-methylbenzyl group, a phenylethyl group, an α-methyl-phenylethyl group, a β-methyl-phenylethyl group, a 3-phenylpropyl group, a 3,3-diphenylpropyl group, a 4-phenylbutyl group, a naphthylmethyl group, a stylyl group, a cynamyl group, a fluolenyl group, a 1-benzocyclobutenyl group, a 1,2,3,4-tetrahydronaphthyl group, an indanyl group, a pyperonyl group, and a pyrenemethyl group; among these, the benzyl group, the phenyl-cyclopentylmethyl group, an α-methylbenzyl group, the phenylethyl group, an α-methyl-phenylethyl group, the β-methyl-phenylethyl group, the 3-phenylpropyl group, the 4-phenylbutyl group, the stylyl group, the cynamyl group, the fluolenyl group, the 1-benzocyclobutenyl group, and the 1,2,3,4-tetrahydronaphthyl group are more preferable; and further, the benzyl group, an α-methylbenzyl group, the phenylethyl group, an α-methyl-phenylethyl group, the β-methyl-phenylethyl group, the 3-phenylpropyl group, the stylyl group, the cynamyl group, the fluolenyl group, the 1-benzocyclobutenyl group, and the 1,2,3,4-tetrahydronaphthyl group are particularly preferable.

Preferable examples of the heterocycle which is formed by $R^1$ and $R^2$ together with a jointly bonded nitrogen atom include a 2-methylaziridine ring, an azetizine ring, a pyrrolidine ring, a 3-pyrroline ring, a piperridine ring, a 1,2,3,6-tetrahydropiridine ring, a hexamethyleneimine ring, a piperadine ring, a 1,3,3-trimethyl-6-azabicyclo[3,2,1]octane ring, a decahydroquinoline ring, an oxazolidine ring, a morpholine ring, a thiazolidine ring, a thiomorpholine ring, an indoline ring, an isoindoline ring, a 1,2,3,4-tetrahydrocarbazole ring, a 1,2,3,4-tetrahydroquinoline ring, a 1,2,3,4-tetrahydroisoquinoline ring, an iminodibenzyl ring, a phenoxadine ring, a phenothiadine ring, a phenadine ring, and the like; among them, the pyrrolidine ring, the 3-pyrroline ring, the piperridine ring, the 1,2,3,6-tetrahydropiridine ring, the hexamethyleneimine ring, the piperadine ring, the decahydroquinoline ring, an oxazolidine ring, the morpholine ring, the thiazolidine ring, the thiomorpholine ring, and the like are more preferable; and further, the pyrrolidine ring, the 3-pyrroline ring, the piperridine ring, the 1,2,3,6-tetrahydropiridine ring, the piperadine ring, the decahydroquinoline ring, an oxazolidine ring, the morpholine ring, the thiazolidine ring, the thiomorpholine ring, and the like are particularly preferable.

The group that is represented by $R^1$ and $R^2$ may include an ether group. Preferable examples of the group that is represented by $R^1$ and $R^2$ may further include a tetrahydrofurfuryl group, a tetrahydropyranylmethyl group, a 2,5-dihydro-2,5-dimethoxyfurfuryl group, and the like.

Preferable examples of the substituent of the alkyl group, the alkenyl group, the aryl group, and the aralkyl group which are represented by $R^1$ and $R^2$, as well as the substituent of the heterocycle which is formed by $R^1$ and $R^2$ together with a jointly bonded nitrogen atom in Formula (I) include an acyl group, an acetyl group, an acylamino group, an acylaminocarbonylamino group, an aralkylaminocarbonylamino group, an allylaminocarbonylamino group, a methacryloylaminocarbonylamino group, a trifluoromethyl group, a fluoro group, a chloro group, a bromo group, an iodo group, a hydroxy group, a nitro group, a methyl group, an ethyl group, an n-propyl group, an i-propyl group, an n-butyl group, an i-butyl group, a sec-butyl group, a t-butyl group, a pentyl group, a hexyl group, a heptyl group, an octyl group, a vinyl group, a methoxy group, an ethoxy group, a buthoxy group, an isopropoxy group, a t-buthoxy group, a cyclohexyloxy group, a vinyloxy group, a methylthio group, an ethylthio group, a pirrolidinyl group, a pipelidinyl group, an amino group, a dimethylamino group, a diethylamino group, a phenyl group, and the like; among these, the acyl group, the acetyl group, the acylamino group, the trifluoromethyl group, the fluoro group, the chloro group, the bromo group, the hydroxy group, the nitro group, the methyl group, the ethyl group, the n-propyl group, the i-propyl group, the n-butyl group, the i-butyl group, the sec-butyl group, the t-butyl group, the pentyl group, the hexyl group, the vinyl group, the methoxy group, the ethoxy group, the buthoxy group, the isopropoxy group, the t-buthoxy group, the cyclohexyloxy group, the vinyloxy group, the methylthio group, the ethylthio group, the pirrolidinyl group, the pipelidinyl group, the amino group, the dimethylamino group, the diethylamino group, the phenyl group, and the like are more preferable; and further the acyl group, the acetyl group, the acylamino group, the trifluoromethyl group, the fluoro group, the chloro group, the bromo group, the hydroxy group, the nitro group, the methyl group, the ethyl group, the n-propyl group, the i-propyl group, the n-butyl group, the i-butyl group, the t-butyl group, the hexyl group, the vinyl group, the methoxy group, the ethoxy group, the isopropoxy group, the cyclohexyloxy group, the vinyloxy group, the methylthio group, the ethylthio group, the pirrolidinyl group, the pipelidinyl group, the amino group, the dimethylamino group, the diethylamino group, the phenyl group, and the like are particularly preferable.

These Substituents May be Further Substituted by Similar Substituents.

In addition, when the substituent of $R^1$ and $R^2$, as well as the substituent of the above-mentioned heterocycles are specifically a group having an active hydrogen, such as a hydroxy group or an amino group, they may be reacted with various acid chlorides, acid anhydrides, halides, or various isocyanates such that they are substituted by an acetyl group, an acyl group, (meth)acryloyl group, an alkylaminocarbonyl group, an arylaminocarbonyl group (for example, a butylaminocarbonyl group, a phenylaminocarbonyl group, and the like), an alkyl group, an aralkyl group, or the like.

In addition, the alkyl group, the alkenyl group, the aryl group, the aralkyl group, and the above-mentioned heterocycles may be further substituted by a group which is similar to that represented by $R^1$ and $R^2$.

From the viewpoint of color value, a total molecular weight of the group which is represented by $R^1$ and $R^2$ (a molecular weight as the sum of a molecular weight of $R^1$ and a molecular weight of $R^2$) is preferably 500 or less; is more preferably 400 or less; and is particularly preferably 300 or less.

A total number of substituents which substitute $R^1$ and $R^2$ is preferably 0 to 4; is more preferably 0 to 3; and is particularly preferably 0 to 2.

The above-mentioned $R^3$ represents a halogen atom, a trihalomethyl group, an alkoxy group having 1 to 21 carbon atoms, a nitro group, or an amino group. The amino group may have a substituent. n represents an integer of 0 to 4.

Preferable examples of $R^3$ include a fluorine atom, a chlorine atom, a bromine atom, a trifluoromethyl group, an alkoxy group having 1 to 15 carbon atoms, a nitro group, and an amino group which may have a substituent; among these, the fluorine atom, the chlorine atom, the trifluoromethyl group, the alkoxy group having 1 to 10 carbon atoms, the nitro group, and the amino group which may have a substituent are more preferable; and further, the chlorine atom, the trifluoromethyl group, the alkoxy group having 1 to 7 carbon atoms, the nitro group, and the amino group which may have a substituent are particularly preferable.

Preferable examples of the alkoxy group that has 1 to 21 carbon atoms and that is represented by $R^3$ include an alkyloxy group, the alkyl portion of which is an alkyl group which is similar to those described as a preferable example of the alkyl group represented by $R^1$ or $R^2$.

Examples of the substituent which may substitute the amino group represented by $R^3$ include a group which is similar to those described as a substituent of the group represented by $R^1$ or $R^2$, and the preferable examples thereof are similar.

n in Formula (I) is an integer that is preferably selected from 0 to 3, more preferably from 0 to 2, and particularly preferably from 0 to 1.

$R^4$ in Formula (I) represents a halogen atom or an —$SO_3M$ group. Preferable examples of $R^4$ include a fluorine atom, a chlorine atom, a bromine atom, and an —$SO_3M$ group. More preferable examples of $R^4$ include a fluorine atom, a chlorine atom, and an —$SO_3M$ group; and particularly preferable examples of $R^4$ include a chlorine atom and an —$SO_3M$ group.

M in Formula (I) represents a hydrogen atom, a cation of a metallic atom or a cation consisting of a nitrogen-containing compound. Among them, specific and preferable examples of M include a hydrogen atom, a cation of a metallic atom (such as a cation of Li, Na, K, Rb, Cs, Ag, Mg, Ca, Sr, Ba, Zn, Al, Ni, Cu, Co, or Fe), and a cation consisting of a nitrogen-containing compound. More preferable examples of M include a hydrogen atom, a cation of Na, K, Rb, Cs, Ag, Mg, Ca, Sr, Ba, Zn, Al, Cu, or Fe, and a cation consisting of a nitrogen-containing compound. Particularly preferable examples of M include a hydrogen atom, a cation of Na, K, Mg, Ca, Ba, Sr, Zn, Al, Cu, or Fe, and a cation consisting of a nitrogen-containing compound.

m in Formula (I) is an integer that is preferably selected from 0 to 4, and more preferably selected from 0 to 3.

A cation represented by the above-mentioned M that consists of a nitrogen-containing compound is selected in consideration of all the factors such as a solubility in organic solvent or water, salt forming properties, absorbance/color value of the dye, and heat resistance and light resistance as a colorant. When the selection is carried out only from the viewpoint of absorbance/color value, the nitrogen-containing compound preferably has the lowest possible molecular weight. Specifically, a molecular weight of 300 or less is preferable; a molecular weight of 280 or less is more preferable; and a molecular weight of 250 or less is particularly preferable.

Specific examples of the cation consisting of the above-mentioned nitrogen-containing compound will be mentioned below, but the cation is not limited to these. The cation of the following nitrogen-containing compounds is formed by protonation of the following.

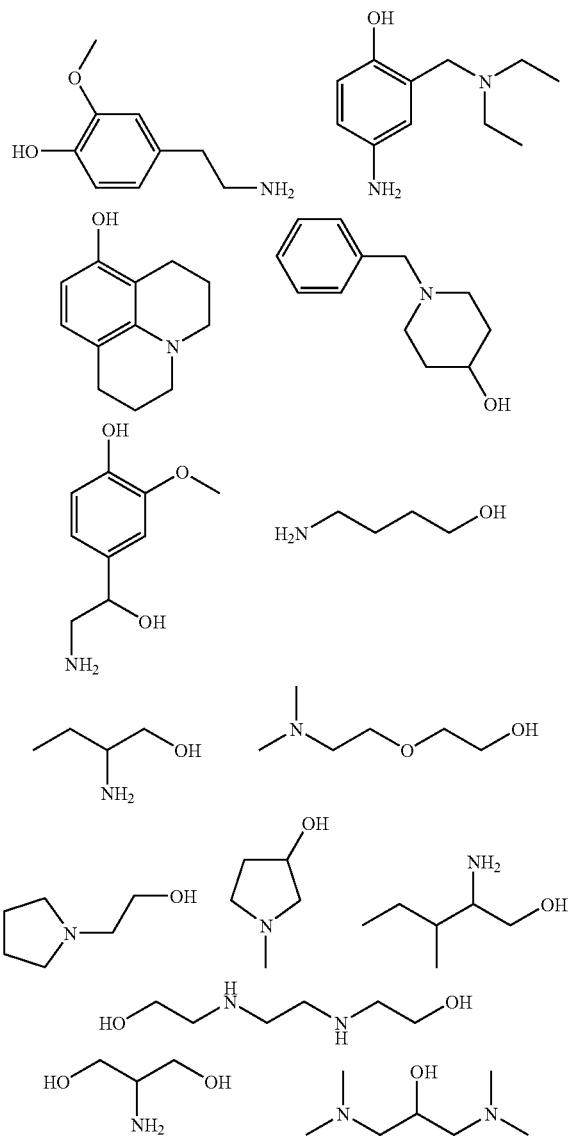

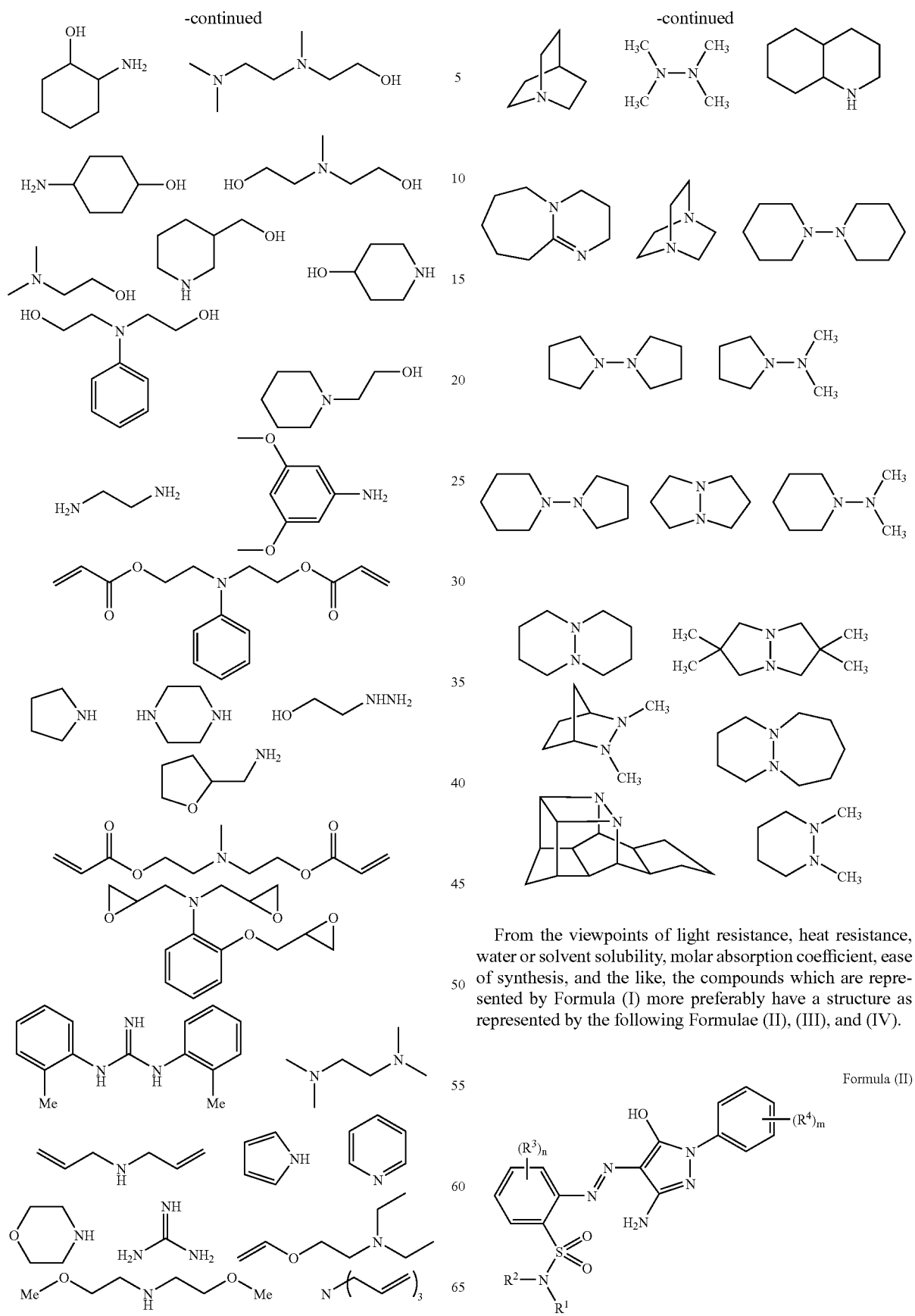
From the viewpoints of light resistance, heat resistance, water or solvent solubility, molar absorption coefficient, ease of synthesis, and the like, the compounds which are represented by Formula (I) more preferably have a structure as represented by the following Formulae (II), (III), and (IV).

-continued

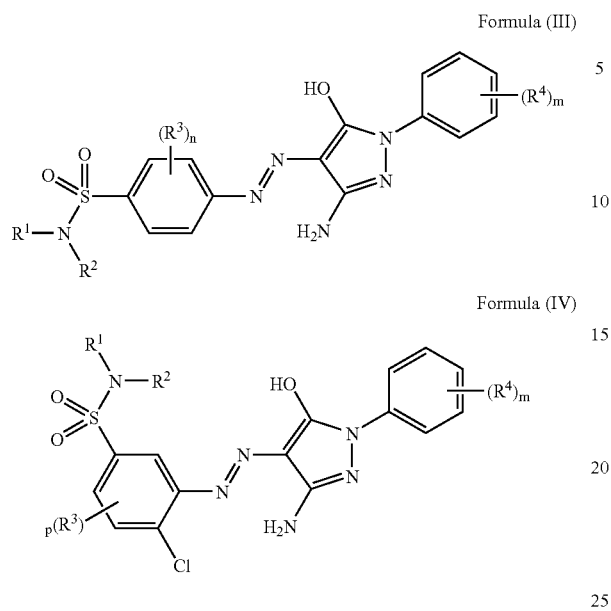

Formula (III)

Formula (IV)

In Formulae (II), (III), and (IV), $R^1$, $R^2$, $R^3$, n, $R^4$, and m represent the same meanings as in Formula (I), and the preferable ranges thereof are the same as given above. In Formula (IV), p represents an integer of 0 to 3.

The following exemplary compounds (1) to (30) provide specific examples of the compounds represented by Formula (I), but the present invention is not limited to these.

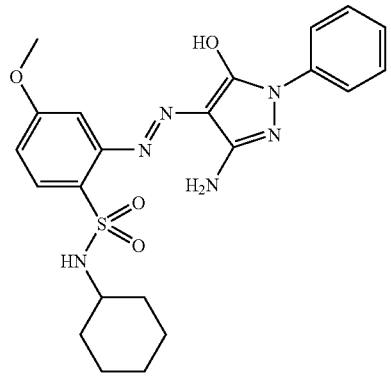

(1)

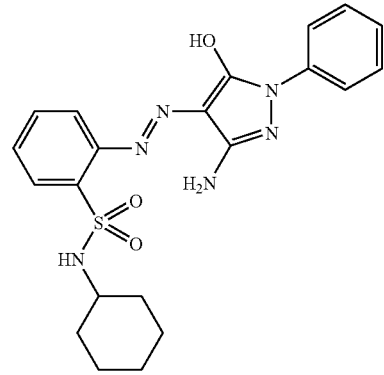

(2)

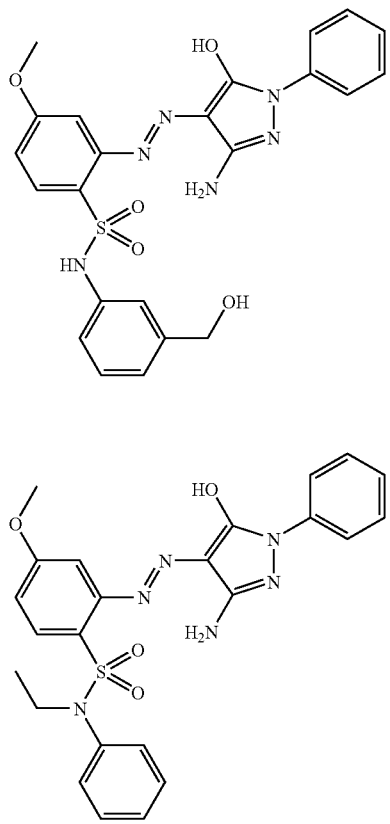

(3)

(4)

(5)

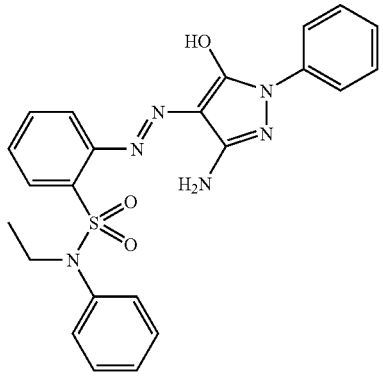

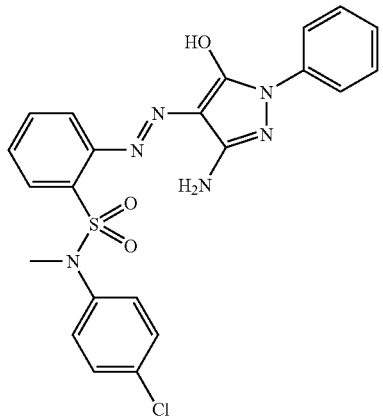

(6)

-continued
(7)
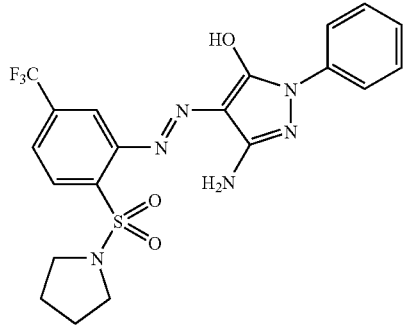
(8)
(9)
(10)
-continued
(11)
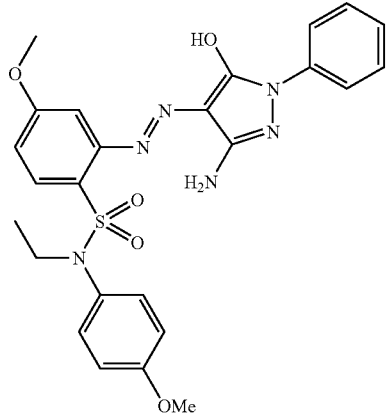
(12)
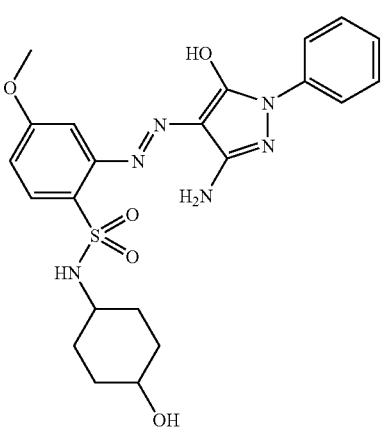
(13)
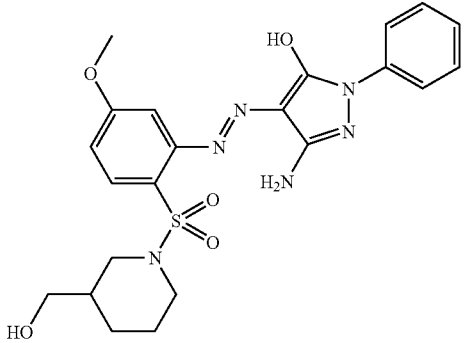
(14)
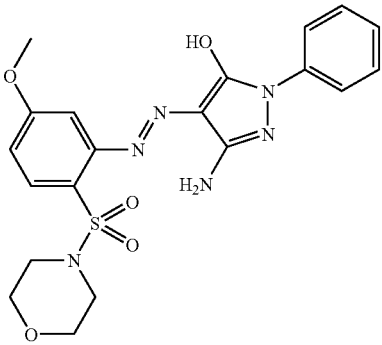

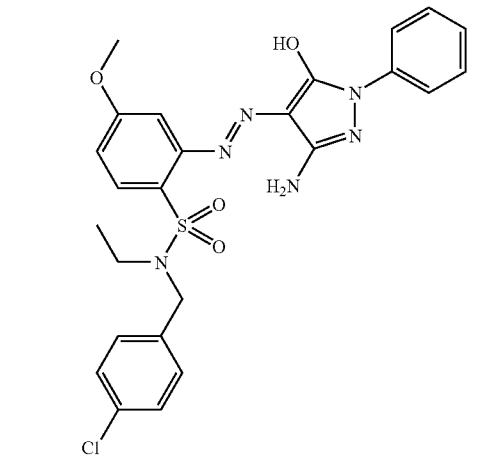
(15)
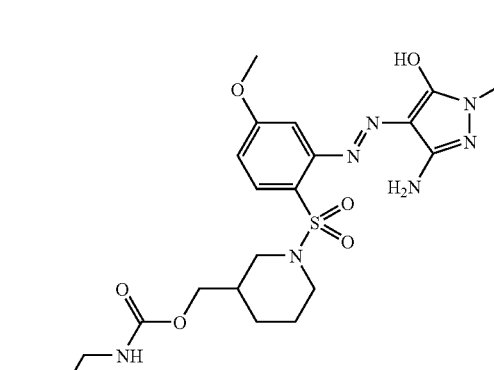
(16)
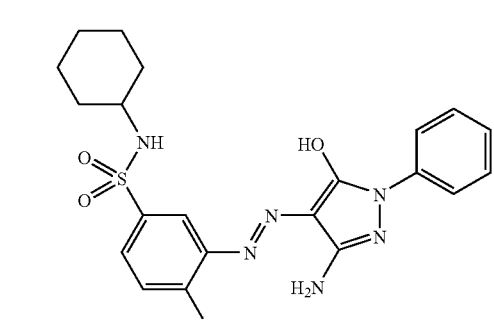
(17)
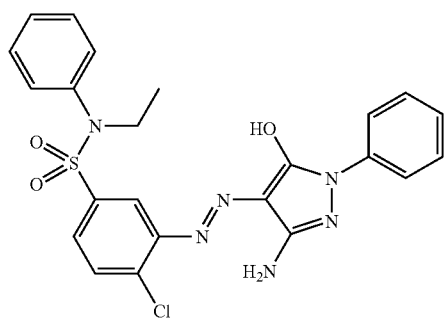
(18)
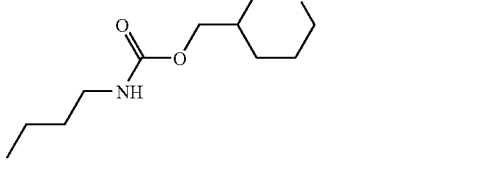
(19)
(20)
(21)
(22)
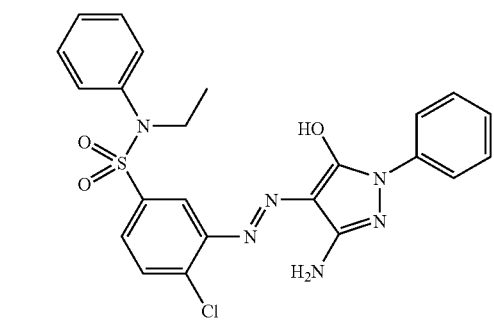
(23)

-continued

(24)
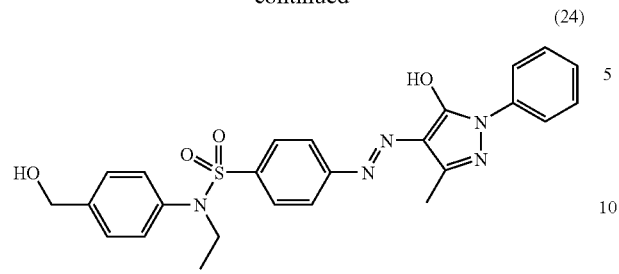

(25)
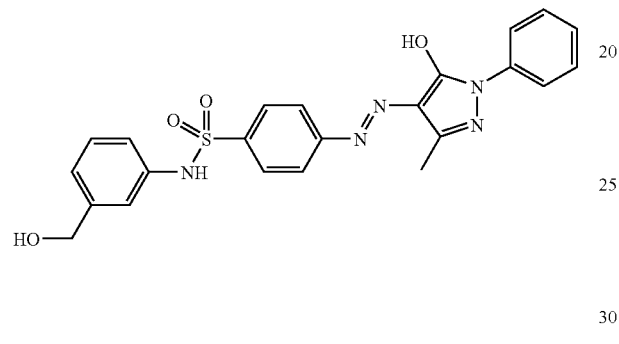

(26)
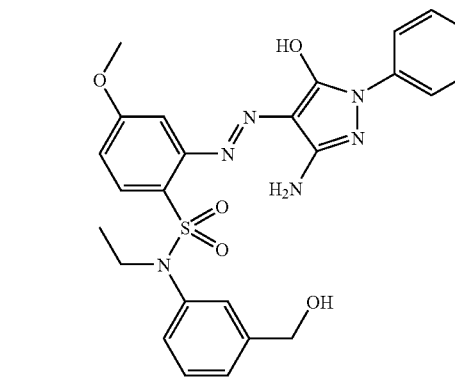

(27)
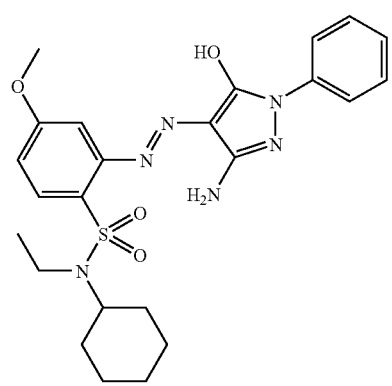

-continued

(28)
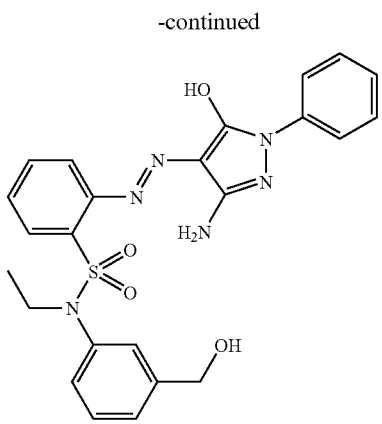

(29)
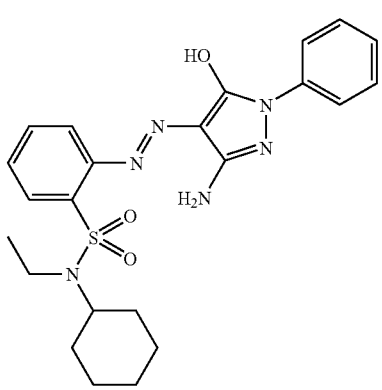

(30)
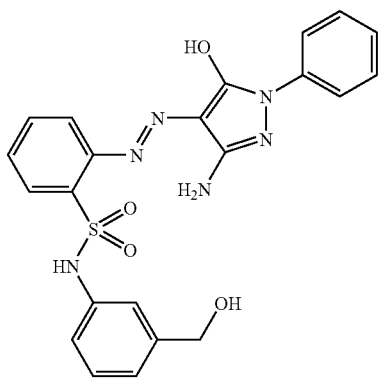

The colorant represented by Formula (I) may be used in combination with a compound of the same species that is represented by Formula (I), and may be simultaneously used with another colorant, a salt formed from another colorant and a metal or a nitrogen-containing compound, a complex, a derivative of another colorant, or the like.

Examples of the another colorant include direct dyes, acidic dyes, mordant/acidic mordant dyes, basic dyes, vat dyes, sulfide dyes, azoic dyes, dispersed dyes, reactive dyes, fluorescent whitening agents, other dyes, pigment resin colors, pigments, and the like which are commonly-known, being given in Colour Index (Society of Dyes and Colorists) and "Dyeing Note" (issued by Shikisensha Co., Ltd.).

Examples of these colorants include CI Solvent Blue 25, CI Solvent Blue 55, CI Solvent Blue 67, CI Solvent Blue 38, CI Solvent Yellow 82, CI Solvent Yellow 162, CI Solvent Orange 56, CI Acid Violet 17, CI Acid Violet 49, CI Direct Blue 86 and the like, and these may be used alone or in mixture of two or more, respectively.

Acidic Dyes

Here is a description about the above-mentioned acidic dyes. The acidic dyes are not particularly limited, provided that they have an acid group, such as the sulfonic acid group or the carboxylic acid group, but an appropriate one of them is selected in consideration of all the necessary performances, such as a solubility in organic solvent and developing solution, a salt formability, an absorbance, an interaction with other components in the curable composition, a light resistance, and a heat resistance.

Specific examples of the above-mentioned acidic dyes are given below, but not limited to these. The examples include: acid alizarin violet N; acid black 1, 2, 24 or 48; acid blue 1, 7, 9, 15, 18, 23, 25, 27, 29, 40, 45, 62, 70, 74, 80, 83, 86, 87, 90, 92, 103, 108, 112, 113, 120, 129, 138, 147, 158, 171, 182, 192, or 249; acid chrome violet K; acid Fuchsin; acid green 1, 3, 5, 9, 16, 25, 27, or 50; acid orange 6, 7, 8, 10, 12, 50, 51, 52, 56, 63, 74, or 95; acid red 1, 4, 8, 14, 17, 18, 26, 27, 29, 31, 34, 35, 37, 42, 44, 50, 51, 52, 57, 66, 73, 80, 87, 88, 91, 92, 94, 97, 103, 111, 114, 129, 133, 134, 138, 143, 145, 150, 151, 158, 176, 183, 198, 211, 215, 216, 217, 249, 252, 257, 260, 266, or 274; acid violet 6B, 7, 9, 17, or 19; acid yellow 1, 3, 7, 9, 11, 17, 23, 25, 29, 34, 36, 40, 42, 54, 65, 72, 73, 76, 79, 98, 99, 111, 112, 114, 116, 169, or 243; Food Yellow 3; and derivatives of these dyes.

Among these, as the above-mentioned acidic dyes, the dyes, such as: acid black 24; acid blue 7, 23, 25, 29, 62, 83, 86, 87, 90, 92, 108, 138, 158, or 249; acid green 3, 5, 9, 16, 25, 27, or 50; acid orange 8, 51, 56, 74, 63, or 74; acid red 1, 4, 8, 34, 37, 42, 52, 57, 80, 97, 114, 143, 145, 151, 183, or 217; acid violet 7; acid yellow 17, 23, 25, 29, 34, 40, 42, 72, 76, 99, 111, 112, 114, 116, 169, 243; Food Yellow 3; and derivatives of these dyes are preferable.

In addition, azo, xanthene, and phthalocyanine acidic dyes other than those mentioned above are preferable, and the acidic dyes, such as CI Solvent Blue 44 or 38; CI Solvent Orange 45, Rhodamine B; Rhodamine 110; and 2,7-naphthalenedisufonic acid, 3-[5-chloro-2-phenoxyphenyl)hydrazono]-3,4-dihydro4-oxo-5-[(phenylsulfonyl)amino]-2,7-naphthalenedisufonic acid, and the derivatives of these dyes are preferably used.

As the derivatives of the above-mentioned acidic dyes, compounds which are produced by converting the sulfonic acid of the acidic dyes into a sulfonamide or a sulfonate, and the like can be effectively used.

Atomic Group that Form Salts with Acidic Dyes

For the atomic group for forming a salt with the above-mentioned acidic dyes, there is no limitation, provided that the atomic group is a cationic one which forms a salt with the anion of the above-mentioned acidic dyes. Examples of such an atomic group include cations consisting of Li, Na, K, Rb, Cs, Ag, Mg, Ca, Sr, Ba, Zn, Al, Ni, Cu, Co, Fe, or a nitrogen-containing compound, and the like.

Here is a description of the nitrogen-containing compounds for forming a salt with the above-mentioned acidic dyes. In the present invention, the nitrogen-containing compound which forms a salt with the acidic dyes is selected by consideration of all the factors, such as the solubility in organic solvent and developing solution, the salt forming properties, the absorbance of the dye, and the interaction with other components in the curable composition. When the selection is carried out only from the viewpoint of absorbance, the above-mentioned nitrogen-containing compound preferably has the lowest possible molecular weight. Specifically, a molecular weight of 245 or less is preferable; a molecular weight of 240 or less is more preferable; and a molecular weight of 230 or less is particularly preferable.

In order to prevent photofading and improve the heat resistance of the dye, generally known nitrogen-containing color fading inhibitor compounds may be used. From this viewpoint, a compound having a low oxidation potential (a low ionization potential), a tertiary amine compound, an aliphatic cyclic amine compound, an aniline compound, a hydrazine compound, and the like are preferable.

The preferable specific examples of the nitrogen-containing compound are the same as those mentioned as M of the —$SO_3M$ in the description of $R^4$ of the above-mentioned Formula (I).

Molar ratio (L) between the atomic group forming a salt with a compound of the Formula (I) (or an acidic dye) and the compound of the Formula (I) (or the acidic dye)

Here is an explanation of the ratio between the number of moles of an atomic group which forms a salt with a compound of the Formula (I) (or an acidic dye) and the number of moles of the compound of the Formula (I) (or the acidic dye) (hereinafter the ratio may be referred to as "L"). The above-mentioned L is a value determining the ratio of the moles of the acidic dye molecules to the moles of the atomic group, which is its counter ion, and can be freely selected in accordance with the salt forming conditions of the acidic dye and atomic group. Specifically, the L is a numerical value in a range of $0 < L \leq 10$, and is the number of acid functional groups in the acidic dye. It is selected in consideration of all the factors, such as the solubility in organic solvent and developing solution, the salt forming properties, the absorbance, the interaction with other components in the curable composition, the light resistance, and the heat resistance. When the selection is carried out only from the viewpoint of absorbance, it is preferable for the above-mentioned L to take a numerical value of $0 < L \leq 7$; it is more preferable for the above-mentioned L to take a numerical value of $0 < L \leq 6$; and it is particularly preferable for the above-mentioned L to take a numerical value of $0 < L \leq 5$.

Concentration Used

Here is an explanation of the concentration used of the compound represented by the Formula (I) (when another dye, such as an acidic dye, is used in conjunction then it is included). The concentration of the compound represented by the Formula (I) (when the above-mentioned acidic dye is used in conjunction then it is included) in the total solid content of the colorant-containing curable composition of the present invention varies depending upon the species of the dye. However, from the viewpoints of curability, developability, pattern configuration, and color intermingling, 0.5 to 80% by mass is preferable; 0.5 to 60% by mass is more preferable; and 0.5 to 50% by mass is particularly preferable.

Binder

The binder used in the present invention is not particularly limited, provided that it is alkali soluble, however, it is preferable to select the binder from the viewpoints of heat resistance, developability, availability, and the like.

As the alkali soluble binder, a binder which is a linear high polymeric organic substance, is soluble in organic solvent, and can be processed for developement with a weak alkali aqueous solution is preferable. Examples of such a linear high polymeric organic substance include polymers which have carboxylic acid in its side chain, such as the methacrylic acid copolymer, the acrylic acid copolymer, the itaconic acid copolymer, the crotonic acid copolymer, the maleic acid copolymer, the partially esterified maleic acid copolymer, and the like as disclosed in, for example, Japanese Patent Application Laid-pen (JP-A) Nos. 59-44615, 54-34327, 58-12577, 54-25957, 59-53836, and 59-71048. Similarly, acidic cellulose derivatives which have carboxylic acid in its side chain are useful. In addition to these, a polymer with a hydroxyl group to which an acid anhydride is added, polyhydroxystyrene resins, polysiloxan resins, poly(2-hydroxyethyl (meth)acrylate), polyvinyl pyrrolidone, polyethylene oxide, polyvinyl alcohol, and the like are also useful.

The above-mentioned alkali soluble binder may be a copolymer of monomers having a hydrophilic property, which examples include alcoxyalkyl(meth)acrylate, hydroxyalkyl(meth)acrylate, glycerol(meth)acrylate, (meth)acrylamide, N-methylol acrylamide, secondary or tertiary alkylacrylamide, dialkylaminoalkyl(meth)acrylate, morpholine(meth)acrylate, N-vinyl pirrolidone, N-vinyl caprolactam, vinyl imidazole, vinyl triazole, methyl(meth)acrylate, ethyl(meth)acrylate, branched or straight-chain propyl(meth)acrylate, branched or straight-chain butyl(meth)acrylate, and phenoxyhydroxypropyl(meth)acrylate, and the like.

As other monomers having a hydrophilic property, monomers and the like including a tetrahydrofurfuryl group, phosphoric acid, phosphate ester, quarternary ammonium salt, ethyleneoxy chain, propyleneoxy chain, sulfonic acid and its salt, morpholinoethyl group, and the like are also useful.

Further, in view of improving a crosslinking efficiency, a polymerizable group may be included in the side chain, and polymers and the like which contain an allyl group, a (meta) acryl group, an allyloxyalkyl group, or the like in the side chain thereof are also useful. Examples of the polymers containing these polymerizable groups are given below, but not limited to these, provided that an alkali soluble group, such as a —COOH group, a —OH group, and an ammonium group, and a carbon-carbon unsaturated bond, are included therein.

For example, a compound which is obtained by reacting a compound having an epoxy ring, which has a reactivity with a —OH group, and a compound having a carbon-carbon unsaturated bond group, such as glycidyl acrylate, with a copolymer which is composed of a monomer having a —OH group, such as 2-hydroxyethylacrylate, a monomer having a —COOH group, such as methacrylic acid, and a monomer which is copolymerizable with the monomer having a —OH group and the monomer having a —COOH group, such as an acryl compound, a vinyl compound or the like, can be used. For the reaction with the —OH group, a compound having an acid anhydride, an isocyanate group, and an acryloyl group can be used in place of the epoxy ring. Further, a reaction product which is obtained by reacting a saturated- or unsaturated-polybasic acid anhydride with a compound obtained by reacting a compound having an epoxy ring with an unsaturated carboxylic acid, such as acrylic acid, as disclosed in Japanese Patent Application Laid-Open (JP-A) No. 6-102669 and 6-1938 can also be used.

Examples of a compound which has both an alkali soluble group, such as a —COOH group, and a carbon-to-carbon unsaturated group include DIANAL NR series (trade name, manufactured by Mitsubishi Rayon Co., Ltd.), —COOH group containing polyurethane acrylic oligomer (trade name: PHOTOMER 6173, manufactured by Diamond Shamlock Co., Ltd.), VISCOTE R-264 and KS RESIST 106 (both trade names, manufactured by Osaka Organic Chemical Industry Ltd.), CYCLOMER P series and PRAXEL CF200 series (both trade names, manufactured by Daicel Company Ltd.), EBECRYL 3800 (trade name, manufactured by Daicel-UCB Company Ltd.), and the like.

Among these various kinds of binders, preferable examples of the alkali soluble binder to be used in the present invention from the viewpoint of heat resistance include a polyhydroxystyrene resin, polysiloxane resin, (meth)acryl resin, acrylamide resin, and acryl/acrylamide copolymer resin, and particularly preferable examples (meth)acryl resin, polyhydroxystyrene resin, and polysiloxane resin of the alkali soluble binder to be used in the present invention. In addition, from the viewpoint of control of developability, a (meth)acryl resin, acrylamide resin, and acryl/acrylamide copolymer resin are preferable. As the (meth)acrylic resin, a copolymer consisting of monomers selected from a benzyl (meth)acrylate, (meth)acryl acid, hydroxyethyl (meth)acrylate, (meth)acrylamide and the like, (meth)acrylic resins having a polymerizable side-chain, such as CYCLOMER P series, PRAXEL CF200 series (both trade names, manufactured by Daicel Company Ltd.), EBECRYL 3800 (trade name, manufactured by Daicel-UCB Company Ltd.), DIANAL NR series (trade name, manufactured by Mitsubishi Rayon Co., Ltd.), VISCOTE R264, KS RESIST 106 (both trade names, manufactured by Osaka Organic Chemical Industry Ltd.), or the like are preferable.

In addition, in view of enhancing a strength of a cured film, alcohol-soluble nylon, polyether formed from 2,2-bis-(4-hydroxyphenyl)-propane and epichlorhydrine, and the like are also useful.

In addition, examples of the binder to be used in the present invention include an alkali soluble phenolic resin. The alkali soluble phenolic resin can be preferably used when the composition of the present invention is rendered to be a positive composition. Examples of the alkali soluble phenolic resin include a novolak resin, a vinyl copolymer, and the like.

Examples of the novolak resin include a novolak resin which is obtained by condensing phenols and aldehydes in the presence of an acidic catalyst. Examples of the phenols include a phenol, crezol, ethyl phenol, butyl phenol, xylenol, phenyl phenol, catechol, rezorcinol, pyrogallol, naphthol, bisphenol A, and the like. The phenols can be used alone or in combination of two or more of them. Examples of the aldehydes include a formaldehyde, paraformaldehyde, acetaldehyde, propyonic aldehyde, benzaldehyde, and the like.

Specific examples of the novolak resin include a condensation product of a metacrezol, paracrezol, or a mixture of these and formalin. A molecular weight distribution of the novolak resin may be adjusted by means such as fractionation. In addition, a low-molecular weight component having a phenolic hydroxyl group, such as bisphenol C or bisphenol A, may be mixed with the above-mentioned novolak resin.

From the viewpoint of developability, liquid viscosity, and the like, the binder is preferably a copolymer having a weight average molecular weight (a polystyrene-converted value measured by the GPC method) of 1,000 to $2\times10^5$, more preferably of 2,000 to $1\times10^5$; and particularly preferably of 3,000 to $5\times10^4$.

From the viewpoint of a developability and the like, an amount of the binder which is used in the composition of the present invention is preferably in a range from 10 to 90% by mass, more preferably in a range from 20 to 80% by mass; and particularly preferably in a range from 30 to 70% by mass relative to the total solid content in the composition of the present invention.

Crosslinking Agent

Next, the crosslinking agent will be described. The present invention mainly use the compound (dye) represented by Formula (I) in order to progress a film curing reaction to a high degree as compared to conventional ones to provide a film having a good curability, however, it is also possible to additionally use a crosslinking agent for obtaining a film which is cured to a still higher degree. The crosslinking agent that can be used in the present invention is not particularly limited, provided that it allows crosslinking reaction for film curing to be carried out, however, preferable examples thereof include: (a) a epoxy resin; (b) a melamine compound, guanamine compound, glycol uryl compound, or urea compound which is substituted by at least one substituent selected from the group consisting of a methylol group, an alkoxymethyl group and an acyloxymethyl group; (c) a phenolic compound, a naphtholic compound, or a hydroxyanthracene compound which is substituted by at least one substituent selected from the group consisting of a methylol group, an alkoxymethyl group and an acyloxymethyl group. Among them, a multifunctional epoxy resin is particularly preferable as the crosslinking agent.

As the (a) epoxy resin, any compounds can be used with no particular restrictions, provided that they have an epoxy group and crosslikability. Examples of these compounds include: low-molecular weight compounds containing a divalent glyidyl group, such as bisphenol-A-diglycidylether, ethyleneglycol diglycidylether, butanediol diglycidylether, hexanediol diglycidylether, dihydroxybiphenyl diglycidylether, phthalic acid diglycidylether, or N,N-diglycidyl aniline; low-molecular weight compounds containing a trivalent glyidyl group, represented by trimethylolpropane triglycidylether, trimethylolphenol triglycidylether, TRISP-PA (trade name, manufactured by Honshu Chemical Industry Co., Ltd.)-triglycidylether, or the like; low-molecular weight compounds containing a tetravalent glycidyl group, represented by pentaerythritol tetraglycidylether, tetramethylol bisphenol-A-tetraglycidylether, or the like; polyvalent low-molecular weight compounds containing a polyvalent glycidyl group, such as dipentaerythritol pentaglycidylether, dipentaerythritol hexaglycidylether, or the like; high-molecular weight compounds containing a glycidyl group, represented by polyglycidyl (meth)acrylate, a 1,2-epoxy-4-(2-oxylanyl)cyclohexane addition product of 2,2-bis(hydroxymethyl)-1-butanol, or the like.

With regard to a number of the methylol group, alkoxymethyl group or acyloxymethyl group which substitutes the (b) compound, the melamine compound is substituted with 2 to 6 of these substituents, and each of the glycoluryl compound, the guanamine compound, and the urea compound is substituted with 2 to 4 of these substituents. It is preferable that the melamine compound is substituted with 5 to 6 of these substituents, and each of the glycoluryl compound, the guanamine compound, and the urea compound is substituted with 3 to 4.

These methylol-group containing compounds can be obtained by heating the alkoxymethyl-group containing compounds in the presence of an acidic catalyst, such as hydrochloric acid, sulfuric acid, nitric acid, or methansulfonic acid, in alcohol. The acyloxymethyl-group containing compound can be obtained by mixing a methylol-group containing compound with acylchloride and mixing them by stirring in the presence of a basic catalyst.

Hereinafter, specific examples of the (b) compound having substituents are mentioned.

Examples of the melamine compound include a hexamethylol melamine, hexamethoxymethyl melamine, compounds in which 1 to 5 methylol groups of hexamethylol melamine are methoxymethylized or mixtures thereof, hexamethoxyethyl melamine, hexaacyloxymethyl melamine, compounds in which 1 to 5 methylol groups of hexamethylol melamine are acyloxymethylized or mixtures thereof, and the like.

Examples of the guanamine compound include tetramethylol guanamine, tetramethoxymethyl guanamine, compounds in which 1 to 3 methylol groups of tetramethylol guanamine are methoxymethylized or mixtures thereof, tetramethoxyethyl guanamine, tetraacyloxymethyl guanamine, compounds in which 1 to 3 methylol groups of tetramethylol guanamine are acyloxymethylized or mixtures thereof, and the like.

Examples of the glycoluryl compound include tetramethylol glycoluryl, tetramethoxymethyl glycoluryl, compounds in which 1 to 3 methylol groups of tetramethylol glycoluryl are methoxymethylized or mixtures thereof, compounds in which 1 to 3 methylol groups of tetramethylol glycoluryl are acyloxymethylized or mixtures thereof, and the like.

Examples of the urea compound include tetramethylol urea, tetramethoxymethyl urea, compounds in which 1 to 3 methylol groups of tetramethylol urea are methoxymethylized or mixtures thereof, tetramethoxyethyl urea, and the like. These may be used alone or in combination of two or more thereof.

The phenolic compound, naphtholic compound, and hydroxyanthracene compound which are categorized as the (c) compound, being substituted by at least one substituent selected from the group consisting of the methylol group, alkoxymethyl group, and acyloxymethyl group suppress intermixing with an overcoated photoresist by a thermal crosslinking, and further enhance a film strength, as are the case with the (b) compound.

It is necessary that one molecule of the compound (c) includes at least two groups of those selected from the group consisting of the methylol groups, alkoxymethyl groups and acyloxymethyl groups. From the viewpoints of thermal crosslinkability and storage stability, it is preferable that the compound (c) is a phenolic compound in which all of the second and fourth positions are substituted.

Further, it is preferable that the naphtholic compound and the hydroxyanthracene compound, which becomes a skeleton of the compound (c), is substituted at all the ortho and para positions thereof by —OH groups.

The third or fifth position of the phenolic compound, which provides a skeleton of the compound (c), may be substituted or unsubstituted. With regard to the naphtholic compound, which provides the skeleton of the compound (c), the positions other than the ortho positions of —OH groups may be substituted or unsubstituted.

The methylol-group containing compounds can be obtained by using a compound with which the ortho or para position (the second or fourth position) relative to the phenolic —OH group is a hydrogen atom as a raw material, and causing it to react with formalin in a presence of a basic catalyst, such as sodium hydroxide, potassium hydroxide, ammonia, or tetraalkyl ammonium hydroxide.

In addition, the alkoxymethyl-group containing compounds can be obtained by heating the methyrol-group containing compounds in a presence of an acidic catalyst, such as hydrochloric acid, sulfuric acid, nitric acid, or methansulfonic acid, in alcohol.

The acyloxymethyl-group containing compounds can be obtained by causing the methyrol-group containing compounds to react with acylchloride in a presence of a basic catalyst.

Examples of the skeleton compound include a phenolic compound, naphthol, and a hydroxyanthracen compound in which ortho or para positions relative to a phenolic —OH group thereof is unsubstituted, and specific examples thereof include a phenol, crezol, isomers thereof, 2,3-xylenol, 2,5-xylenol, 3,4-xylenol, 3,5-xylenol, bisphenols such as bisphenol-A, 4,4'-bishydroxybiphenyl, TRIS P-PA (described above), naphthol, dihydroxynaphthalen, 2,7-dihydroxyanthracen and the like.

Specific examples of the (c) compound include a trimethylol phenol, tri(methoxymethyl)phenol, trimethylol phenol, compounds in which 1 or 2 methylol groups of trimethylol phenol are methoxymethylized, trimethylol-3-crezol, tri(methoxymethyl)-3-crezol, compounds in which 1 or 2 methylol groups of trimethylol-3-crezol are methoxymethylized, dimethylol crezols such as 2,6-dimethylol-4-crezol, tetramethylol bisphenol-A, tetramethoxymethyl bisphenol-A, compounds in which 1 to 3 methylol groups of tetramethylol bisphenol-A are methoxymethylized, tetramethylol-4,4'-bishydroxybiphenyl, tetramethoxymethyl-4,4-bishydroxybiphenyl, hexamethylol species of TRISP-PA (described above), hexamethoxymethyl species TRIS P-PA (described above), compounds in which 1 to 5 methylol groups of hexamethylol species of TRIS P-PA (described above) are methoxymethylized, bishydroxymethyl naphthalenediol, and the like.

Examples of the hydroxyanthracen compound include a 1,6-dihydroxymethyl-2,7-dihydroxyanthracen, and the like.

Examples of the acyloxymethyl-group containing compounds include compounds in which a part or all of the methylol groups of the methylol-group containing compounds are acyloxymethylized.

Among these compounds, a trimethylol phenol, bishydroxymethyl-p-crezol, tetramethylol bisphenol-A, hexamethylol species of TRIS P-PA (described above), or phenolic compounds in which the hexamethylol groups of these compounds are substituted by an alkoxymethyl group and both a methylol group and an alkoxymethyl group.

These May be Used Alone or in Combination of Two or More Thereof.

The content of the compounds (a) to (c) in the colorant-containing curable composition of the present invention varies depending upon the base material, however, from the viewpoints of curability, spectral characteristic, and the like, it is preferably in a range of 1 to 70% by mass, more preferably in a range of 5 to 50% by mass, and particularly preferably in a range of 7 to 30% by mass with respect to the solid content in the composition.

Monomer

Next, the polymerizable compound (hereinafter referred to as "monomer") to be contained when the composition of the present invention is of negative composition will be described. As the monomer, a compound which has at least one addition-polymerizable ethylene group, has a boiling point of 100° C. or higher under normal pressure, and has an ethylenic unsaturated group, is preferable. Examples thereof include: monofunctional acrylates and methacrylates such as polyethylene glycol mono(meth)acrylate, polypropylene glycol mono(meth)acrylate, phenoxyethyl(meth)acrylate; polyethylene glycol di(meth)acrylates; trimethylol ethane tri(meth)acrylates; neopentyl glycol di(meth)acrylates; pentaerythritol tri(meth)acrylates; pentaerythritol tetra(meth)acrylates; dipentaerythritol penta(meth)acrylates; dipentaerythritol hexa(meth)acrylates; hexanediol(meth)acrylates; trimethylol propane tri(acryloyloxypropyl)ether; tri(acryloyloxyethyl)isocyanulate; compounds obtained by adding ethylene oxides, propylene oxides or the like to multifunctional alcohols, such as glycerin or trimethylol ethane, and then (meth)acrylating the resultant of the reaction; urethane acrylates such as those disclosed in Japanese Patent Application Publication (JP-B) Nos. 4841708 and 50-6034 or Japanese Patent Application Laid-Open (JP-A) No. 51-37193; polyester acrylates such as those disclosed in Japanese Patent Application Laid-Open (JP-A) No. 48-64183, Japanese Patent Application Publication (JP-B) Nos. 49-43191 and 52-30490; and multifunctional acrylates or methacrylates, such as epoxyacrylates, which are reaction products of epoxy resins and (metha)acrylic acids, and mixtures thereof. Further, examples thereof includes those introduced as light curable monomers and oligomers in Journal of the Adhesion Society of Japan, Vol. 20, No. 7, pp. 300 to 308.

As the above-mentioned monomer, the (meth)acrylic ester monomer is preferable, and the quadrifunctional or higher (meth)acrylic ester monomer is particularly preferable.

From the viewpoint of curability and the like, the content of the above-mentioned monomer in the composition of the present invention is preferably 0.1 to 90% by mass, more preferably 1.0 to 80% by mass, and particularly preferably 2.0 to 70% by mass with respect to the solid content of the composition.

Photopolymerization Initiator

Next, the photopolymerization initiator to be contained when the composition of the present invention is a negative composition will be described. The photopolymerization initiator is not particularly limited, provided that it allows the monomers having polymerizability to be polymerized, however, it is preferable that the photopolymerization initiator is selected from the viewpoints of characteristics, initiation efficiency, absorption wavelength, availability, cost, and the like.

Examples of the photopolymerization initiator include a trihalomethyltriazine compound, a benzyldimethylketal compound, an α-hydroxyketone compound, an α-aminoketone compound, a phosphine oxide compound, a metalocen compound, an oxime compound, a triallyl imidazole dimer, a benzothiazole compound, a benzophenone compound, an acetophenone compound and its derivative, a cyclopentadien-benzene-ferrous complex and its salt, a halomethyloxadiazole compound, and a 3-aryl-substituted coumarin compound, and the like, and the photopolymerization initiator preferably comprises at least one kind of compound selected from the group consisting of the α-aminoketone compound, the phosphine oxide compound, the metalocen compound, the oxime compound, and the triallyl imidazole dimer.

In addition, it is preferable that the photopolymerization initiator is a compound which does not generate an acid by decomposition.

Examples of the active halogen compound, such as the above-mentioned halomethyloxadiazole compound, include 2-halomethyl-5-vinyl-1,3,4-oxadiazole compound and the like as disclosed in Japanese Patent Application Publication (JP-B) No. 57-6069, 2-trichloromethyl-5-styryl-1,3,4-oxadiazole, 2-trichloromethyl-5-(p-cyanostyryl)-1,3,4-oxadiazole, 2-trichloromethyl-5-(p-methoxystyryl)-1,3,4-oxadiazole, and the like.

Examples of the trihalomethyl-s-triazine compound photopolymerization initiator include vinyl-halomethyl-s-triazine compounds as disclosed in Japanese Patent Application Publication (JP-B) No. 59-1281, 2-(naphtho-1-yl)-4,6-bis-halomethyl-s-triazine compounds and 4-(p-aminophenyl)-2,6-di-halomethyl-s-triazine compounds as disclosed in Japanese Patent Application Laid-pen (JP-A) No. 53-133428, and the like.

Other examples thereof include a 2,4-bis(trichloromethyl)-6-p-methoxystyryl-s-triazine, 2,6-bis(trichloromethyl)-4-3, 4-methylenedioxyphenyl)-1,3,5-triazine, 2,6-bis(trichloromethyl)-4-4-methylphenyl)-1,3,5-triazine, 2,4-bis(trichloromethyl)-6-(1-p-dimethylaminophenyl-1,3-butadienyl)-s-triazine, 2-trichloromethyl-4-amino-6-p-methoxystyryl-s-triazine, 2-(naphtho-1-yl)-4,6-bis-trichloromethyl-s-triazine, 2-(4-ethoxy-naphtho-1-yl)-4,6-bis-trichloromethyl-s-triazine, 2-(4-buthoxy-naphtho-1-yl)-4,6-bis-trichloromethyl-s-triazine, 2-[4-(2-methoxyethyl)-naphtho-1-yl]-4,6-bis-trichloromethyl-s-triazine, 2-[4-2-ethoxyethyl)-naphtho-1-yl]-4,6-bis-trichloromethyl-s-triazine, 2-[4-2-buthoxyethyl)-naphtho-1-yl]-4,6-bistrichloromethyl-s-triazine, 2-(2-methoxy-naphtho-1-yl)-4,6-bis-trichloromethyl-s-triazine, 2-(6-methoxy-5-methyl-naphtho-2-yl)-4,6-bis-trichloromethyl-s-triazine, 2-6-(methoxy-naphtho-2-yl)-4,6-bis-trichloromethyl-s-triazine, 2-(5-methoxy-naphtho-1-yl)-4,6-bis-trichloromethyl-s-triazine, 2-(4,7-dimethoxy-naphtho-1-yl)-4,6-bis-trichloromethyl-s-triazine, 2-(6-ethoxy-naphtho-2-yl)-4,6-bis-trichloromethyl-s-triazine, 2-(4,5-dimethoxy-naphtho-1-yl)-4,6-bis-trichloromethyl-s-triazine, 4-[p-N,N-di(ethoxycarbonylmethyl)aminophenyl]-2,6-di(trichloromethyl)-s-triazine, 4-[o-methyl-N,N-di(ethoxycarbonylmethyl)aminophenyl]-2,6-di(trichloromethyl)-s-triazine, 4-[p-N,N-di(chloroethyl)aminophenyl]-2,6-di(trichloromethyl)-s-triazine, 4-[o-methyl-p-N,N-di(chloroethyl)aminophenyl]-2,6-di(trichloromethyl)-s-triazine, 4-(p-N-chloroethylaminophenyl)-2,6-di(trichloromethyl)-s-triazine, 4-(p-N-ethoxycarbonylmethylaminophenyl)-2,6-di(trichloromethyl)-s-triazine, 4-[p-N,N-di(phenyl)aminophenyl]-2,6-di(trichloromethyl)-s-triazine, 4-(p-N-chloroethylcarbonylaminophenyl)-2,6-di(trichloromethyl)-s-triazine, 4-[p-N-(p-methoxyphenyl)carbonylaminophenyl]-2,6-di(trichloromethyl)-s-triazine, 4-[m-N,N-di(ethoxycarbonylmethyl)aminophenyl]-2,6-di(trichloromethyl)-s-triazine, 4[m-bromo-p-N,N-di(ethoxycarbonylmethyl)aminophenyl]-2,6-di(trichloromethyl)-s-triazine, 4-[m-chloro-p-N,N-di(ethoxycarbonylmethyl)aminophenyl]-2,6-di(trichloromethyl)-s-triazine, 4-[m-fluoro-p-N,N-di(ethoxycarbonylmethyl)aminophenyl]-2,6-di(trichloromethyl)-triazine, 4-[o-bromo-p-N,N-di(ethoxycarbonylmethyl)aminophenyl]-2,6-di(trichloromethyl)-s-triazine, 4-[o-chloro-p-N,N-di(ethoxycarbonylmethyl)aminophenyl]-2,6-di(trichloromethyl)-s-triazine, 4-[o-fluoro-p-N,N-di(ethoxycarbonylmethyl)aminophenyl]-2,6-di(trichloromethyl)-s-triazine, 4-[o-bromo-p-N,N-di(chloroethyl)aminophenyl]-2,6-di(trichloromethyl)-s-triazine, 4-[o-chloro-p-N,N-di(chloroethyl)aminophenyl]-2,6-di(trichloromethyl)-s-triazine, 4-[o-fluoro-p-N,N-di(chloroethyl)aminophenyl]-2,6-di(trichloromethyl)-s-triazine, 4-[m-bromo-p-N,N-di(chloroethyl)aminophenyl]-2,6-di(trichloromethyl)-s-triazine, 4-[m-chloro-p-N,N-di(chloroethyl)aminophenyl]-2,6-di(trichloromethyl)-s-triazine, 4-[m-fluoro-p-N,N-di(chloroethyl)aminophenyl]-2,6-di(trichloromethyl)-s-triazine, 4-(m-bromo-p-N-ethoxycarbonylmethylaminophenyl)-2,6-di(trichloromethyl)-s-triazine, 4-(m-chloro-p-N-ethoxycarbonylmethylaminophenyl)-2,6-di(trichloromethyl)-s-triazine, 4-(m-fluoro-p-N-ethoxycarbonylmethylaminophenyl)-2,6-di(trichloromethyl)-s-triazine, 4-(o-bromo-p-N-ethoxycarbonylmethylaminophenyl)-2,6-di(trichloromethyl)-s-triazine, 4-(o-chloro-p-N-ethoxycarbonylmethylaminophenyl)-2,6-di(trichloromethyl)-s-triazine, 4-(o-fluoro-p-N-ethoxycarbonylmethylaminophenyl)-2,6-di(trichloromethyl)-s-triazine, 4-(m-bromo-p-N-chloroethylaminophenyl)-2,6-di(trichloromethyl)-s-triazine, 4-(m-chloro-p-N-chloroethylaminophenyl)-2,6-di(trichloromethyl)-s-triazine, 4-(m-fluoro-p-N-chloroethylaminophenyl)-2,6-di(trichloromethyl)-s-triazine, 4-(o-bromo-p-N-chloroethylaminophenyl)-2,6-di(trichloromethyl)-s-triazine, 4-(o-chloro-p-N-chloroethylaminophenyl)-2,6-di(trichloromethyl)-s-triazine, 4-(o-fluoro-p-N-chloroethylaminophenyl)-2,6-di(trichloromethyl)-s-triazine, and the like.

In addition to these, TAZ series manufactured by Midori Kagaku Co., Ltd., including TAZ-107, TAZ-110, TAZ-104, TAZ-109, TAZ-140, TAZ-204, TAZ-113, TAZ-123, and TAZ-104 (all trade names, manufactured by Midori Kagaku Co., Ltd.); T series manufactured by Panchim Ltd., including T-OMS, T-BMP, T-R, and T-B (all trade names, manufactured by Panchim Ltd.); IRGACURE® series manufactured by Ciba Specialty Chemicals Inc., including IRGACURE® 651, IRGACURE® 184, IRGACURE® 500, IRGACURE® 1000, IRGACURE® 149, IRGACURE® 819, and IRGACURE® 261; DAROCUR® series manufactured by Ciba Specialty Chemicals Inc., including DAROCUR® 11734; 4'-bis(diethylamino)benzophenone, 2-(o-benzoyloxime)-1-[4-phenylthio)phenyl]-1,2-octanedione, 2-benzyl-2-dimethylamino-4-morpholinobuthylophenone, 2,2-dimethoxy-2-phenylacetophenone, 2-(o-chlorphenyl)-4,5-diphenylimidazolyl dimer, 2-(o-fluorophenyl)-4,5-diphenylimidazolyl dimer, 2-(p-methoxyphenyl)-4,5-diphenylimidazolyl dimer, 2-(p-dimethoxyphenyl)-4,5-diphenylimidazolyl dimer, 2-(2,4-dimethoxyphenyl)-4,5-diphenylimidazolyl dimer, 2-(p-methylmercaptophenyl)-4,5-diphenylimidazolyl dimer, benzoinisopropylether, and the like can be usefully used.

Examples of the α-aminoketone compound include IRGACURE® series manufactured by Ciba Specialty Chemicals Inc. (such as IRGACURE® 907 or IRGACURE® 369), 2-methyl-1-phenyl-2-morpholinopropane-1-on, 2-methyl-1-[4-(hexyl)phenyl]-2-morpholinopropane-1-on, 2-ethyl-2-dimethylamino-1-(4-morpholinophenyl)butanone-1, and the like.

The oxime compound is nor particularly limited, however, preferable examples include 2-O-benzoyloxime)-1-[4-phenylthio)phenyl)-1,2-octanedione, 1-(4-methylsulfanyl-phenyl)butane-1,2-butane-2-oxime-O-acetate, 1-(4-methylsulfanyl-phenyl)-butane-1-onoxime-O-acetate, hydroxyimino-(4-methylsulfanyl-phenyl)-acetic acid ethyl ester-O-acetate, hydroxyimino-(4-methylsulfanyl-phenyl)-acetic acid ethyl ester-O-benzoate, and the like.

In addition, regarding other photopolymerization initiators, preferable examples of the benzylmethylketal compound include IRGACURE® 651; those of the α-hydroxyketone compound include IRGACURE® 184, IRGACURE® 1173, IRGACURE® 500, IRGACURE® 1000, and IRGACURE® 2959; those of the α-aminoketone compound include IRGACURE® 907 and IRGACURE® 369; those of the phosphine oxide compound (blend) include IRGACURE® 1700, IRGACURE® 149, IRGACURE® 1850, IRGACURE® 819, and IRGACURE® 814; those of the metalocen compound include IRGACURE® 784 and IRGACURE® 261 (all manufactured by Ciba Specialty Chemicals Inc.), from the viewpoints of availability and stability, and the analogs/peripheral compounds for these, and the like are also preferable.

As described above, from the viewpoints of light resistance and heat resistance of the dye, it is preferable to use a compound which does not generate an acid by decomposition. Namely, it is preferable to use at least one kind of compound selected from the group consisting of a benzylmethylketal compound, an α-hydroxyketone compound, an α-aminoketone compound, a phosphine oxide compound, a metalocen compound, an oxime compound, a triallylimidazole dimer, a benzothiazole compound, a benzophenone compound, a acetophenone compound and its derivative, and a cyclopentadiene-benzene-ferrous complex and its salt as the compound which does not generate an acid by decomposition. It is further preferable to use at least one kind of compound selected from the group consisting of an α-aminoketone compound, a phosphine oxide compound, a metalocen compound, an oxime compound, and a triallylimidazole dimer.

These photopolymerization initiators can be used in combination with sensitizers and light stabilizers.

Specific examples of the sensitizers and light stabilizers include: benzoin, benzoinmethylether, 9-fluorenone, 2-chloro-9-fluorenone, 2-methyl-9-fluorenone, 9-anthrone, 2-bromo-9-anthrone, 2-ethyl-9-anthrone, 9,10-anthraquinone, 2-ethyl-9,10-anthraquinone, 2-t-butyl-9,10-athraquinone, 2,6-dichloro-9,10-anthraquinone, xanthone, 2-methylxanthone, 2-methoxyxanthone, 2-methoxyxanthone, thioxanthone, 2,4-diethylthioxanthone, acridone, 10-butyl-2-chloroacridone, benzyl, dibenzalacetone, p-dimethylamino)phenylstyrylketone, p-dimethylamino)phenyl-p-methylstyrylketone, benzophenone, p-(dimethylamino)benzophenone (or Michler's ketone), p-(dimethylamino) benzophenone, benzoanthron, and the like; benzothiazole compounds and the like as disclosed in Japanese Patent Application Publication (JP-B) No. 51-48516; TINUVIN® 1130 and TINUVIN® 400 (both manufactured by Ciba Specialty Chemicals); and the like.

In addition to the above-mentioned photopolymerization initiators, commonly-known photopolymerization initiators can be used in the composition of the present invention.

Specific examples thereof include vicinalpolyketolaldonyl compounds as disclosed in U.S. Pat. No. 2,367,660; α-carbonyl compounds as disclosed in U.S. Pat. Nos. 2,367,661 and 2,367,670; acyloinethers as disclosed in U.S. Pat. No. 2,448,828; aromatic acyloin compounds substituted by α-hydrocarbon groups as disclosed in U.S. Pat. No. 2,722,512; multicore quinone compounds as disclosed in U.S. Pat. Nos. 3,046,127 and 2,951,758; combinations of triallylimidazole dimers and p-aminophenylketones as disclosed in U.S. Pat. No. 3,549,367; benzothiazole compounds and trihalomethyl-s-triazine compounds as disclosed in Japanese Patent Application Publication (JP-B) No. 51-48516, and the like.

The amount used of the above-mentioned photopolymerization initiator is preferably 0.01 to 50% by mass, more preferably 1 to 30% by mass, and particularly preferably 1 to 20% by mass with respect to the monomer solid content. When the amount used of the photopolymerization initiator is within the range of 0.01 to 50% by mass, the film strength can be prevented from being weakened for too low molecular weight.

A thermal polymerization inhibitor is preferably added to the composition of the present invention.

Examples of the thermal polymerization inhibitor include hydroquinone, p-methoxyphenol, di-t-butyl-p-crezol, pirrogalol, t-butylcatechol, benzoquinone, 4,4'-thiobis(3-methyl-6-t-butylphenol), 2,2'-methylenebis(4-methyl-6-t-butylphenol), 2-mercaptobenzoimidazole, and the like.

Solvent

The solvent to be used with the present invention is not basically particularly limited, provided that the requirements for solubility and coatability of the composition are met, however, it is preferable that the solvent is selected in consideration of the solubility, coatability, and safety of dyes and binders.

Preferable examples of the solvent to be used in preparing the composition of the present invention includes esters such as ethyl acetate, n-butyl acetate, isobutyl acetate, amyl formate, isoamyl acetate, isobutyl acetate, butyl propionate, isopropyl butyrate, ethyl butyrate, butyl butyrate, alkyl esters, methyl lactate, ethyl lactate, methyl oxyacetate, ethyl oxyacetate, butyl oxyacetate, methoxy methylacetate, methoxy ethylacetate, methoxy butylacetate, ethoxy methylacetate, ethoxy ethylacetate, 3-oxypropionic acid alkyl esters such as methyl 3-oxypropionate or ethyl 3-oxypropionate, methyl 3-methoxypropionate, ethyl 3-methoxypropionate, methyl 3-ethoxypropionate, ethyl 3-ethoxypropionate, methyl 2-oxypropionate, ethyl 2-oxypropionate, propyl 2-oxypropionate, methyl 2-methoxypropionate, ethyl 2-methoxypropionate, propyl 2-methoxypropionate, methyl 2-ethoxypropionate, ethyl 2-ethoxypropionate, methyl 2-oxy-2-methylpropionate, ethyl 2-oxy-2-methylpropionate, methyl 2-methoxy-2-methylpropionate, ethyl 2-ethoxy-2-methylpropionate, methyl pyruvate, ethyl pyruvate, propyl pyruvate, methyl acetoacetate, ethyl acetoacetate, methyl 2-oxobutanate, or ethyl 2-oxobutanate; ethers such as diethylene glycol dimethyl ether, tetrahydrofuran, ethylene glycol monomethyl ether, ethylene glycol monoethyl ether, methyl cellosolve acetate, ethyl cellosolve acetate, diethylene glycol monomethyl ether, diethylene glycol monoethyl ether, diethylene glycol monombutyl ether, propylene glycol methyl ether, propylene glycol methyl ether acetate, propylene glycol ethyl ether acetate, or propylene glycol propyl ether acetate; ketones such as methylethyl ketone, cyclohexane, 2-heptanone, or 3-heptanone; and aromatic hydrocarbons such as toluene and xylene.

Among these, as the solvent to be used in the present invention, methyl 3-ethoxypropionate, ethyl 3-ethoxypropionate, ethyl cellosolve acetate, ethyl lactate, diethylene glycol dimethyl ether, butyl acetate, methyl 3-methoxypropionate, 2-heptanone, cyclohexane, ethyl carbitol acetate, butyl carbitol acetate, propylene glycol methyl ether, propylene glycol methyl ether acetate and the like are more preferable.

Variety of additives, such as fillers, high-molecular compounds other than the above-mentioned ones, surfactants, adherence promotors, oxidization inhibitors, ultraviolet absorbers, aggregation inhibitors and the like can be compounded to the composition of the present invention.

Specific examples of these additives include fillers such as glasses or alumina; high-molecular compounds other than binder resins such as polyvinyl alcohol, polyacrylic acid, polyethylene glycol monoalkyl ether, or polyfluoroalkyl acrylate; surfactants such as nonionic surfactants, cationic surfactants, or anionic surfactants; adhesion promotors such as vinyl trimethoxysilane, vinyl triethoxysilane, vinyl tris(2-methoxyethoxy)silane, N-2-aminoethyl)-3-aminopropylmethyldimethoxysilane, N-(2-aminoethyl)-3-aminopropyltrimethoxysilane, 3-aminopropyltriethoxysilane, 3-glycidoxypropyltrimethoxysilane, 3-glycidoxypropylmethyldimethoxysilane, 2-(3,4-epoxycyclohexyl)ethyltrimethoxysilane, 3-chloropropylmethyldimethoxysilane, 3-chloropropyltrimethoxysilane, 3-methacryloxypropyltrimethoxysilane, or 3-mercaptopropyltrimethoxysilane; oxidation inhibitors such as 2,2-thiobis(4-methyl-6-t-butylphenol) or 2,6-di-t-butylphenol; ultraviolet absorbers such as 2-(3-t-butyl-5-methyl-2-hydroxyphenol)-5-chlorobenzotriazole or alcoxybenzophenone; and aggregation inhibitors such as sodium polyacrylate.

Further, when a promotion of an alkali solubility of a radiation unirradiated portion is intended for further improvement in a developability of the composition of the present invention, an organic carboxylic acid, preferably a low-molecular weight organic carboxylic acid having a molecular weight of 1000 or less, can be added to the composition of the present invention. Specific examples of the organic carboxylic acid include aliphatic monocarboxylic acids such as formic acid, acetic acid, propionic acid, lactic acid, valeric acid, pivalic acid, caproic acid, diethylacetic acid, enanthic acid, or caprylic acid; aliphatic dicarboxylic acids such as oxalic acid, malonic acid, succinic acid, glutaric acid, adipic acid, pimelic acid, suberic acid, azelaic acid, sebacic acid, brasylic acid, methylmalonic acid, dimethylmalonic acid, methylsuccinic acid, tetramethylsuccinic acid, or citraconic acid; aliphatic tricarboxylic acids such as tricarballylic acid, aconitic acid, or camphoronic acid; aromatic monocarboxylic acids such as benzoic acid, toluic acid, cuminic acid, hemellitic acid, or mesitylenic acid; aromatic polycarboxylic acids such as phthalic acid, isophthalic acid, terephthalic acid, trimellitic acid, trimesic acid, mellophanic acid, or pyromellitic acid; and other carboxylic acids such as phenylacetic acid, hydratropic acid, hydrocinnamic acid, mandelic acid, phenylsuccinic acid, atropic acid, cinnamic acid, methyl cinnamate, benzyl cinnamate, cinnamylidene acetic acid, coumaric acid, or unbellic acid.

Positive Composition

In order to obtain a positive image, in other words, when the composition of the present invention is a positive composition, the composition of the present invention contains a sensitizer in combination with a solvent. Preferable examples of the sensitizer include naphthoquinonediazide compounds. Further, the colorant-containing curable positive composition may contain a curing agent.

Examples of the above-mentioned naphthoquinonediazide compound include o-benzoquinonediazide sulfonic acid ester and o-naphthoquinonediazide sulfonic acid ester.

Specific examples thereof include o-naphthoquinonediazide-5-sulfonic acid ester, o-naphthoquinonediazide-5-sulfonic acid amide, o-naphthoquinonediazide-4-sulfonic acid ester, o-naphthoquinonediazide-4-sulfonic acid amide, and the like. These esters and amide compounds can be manufactured by commonly-known methods such as those disclosed in Japanese Patent Application Laid-Open (JP-A) Nos. 2-84650 or 349437, which use phenolic compounds represented by "Formula (I)".

When the composition of the present invention is a positive composition, the above-mentioned alkali soluble phenolic resin and the above-mentioned curing agent are generally preferably dissolved in the organic solvent at a rate of about 2 to 50% by mass and about 2 to 30% by mass respectively. The above-mentioned naphthoquinonediazide compound and that of the above-mentioned organic solvent soluble dye are generally preferably added to the solution in which the above-mentioned alkali soluble resin and curing agent are dissolved, at a rate of about 2 to 30% by mass and about 2 to 50% by mass respectively, from the viewpoints of curability, spectral characteristic, and the like.

Preferable examples of the above-mentioned curing agent include the melamine compounds, the methylol-group containing compounds and the like which are mentioned above as the crosslinking agents.

When the composition of the present invention is a positive composition, alkali soluble resins may be used by being mixed therein, and examples of the alkali soluble resins include novolak resins, vinyl phenolic resins, and the like.

Further, when the colorant-containing curable composition of the present invention is configured to be a positive composition, it can be configured by including a compound represented by the above-mentioned Formula (I), a photo-acid generator, and a curing agent.

The photo-acid generator is not particularly limited, provided that it is a compound which generates an acid when exposed to light, however, preferable examples thereof include various oxime compounds such as α-(4-toluenesulfonyloxyimino)phenylacetonitrile, various iodonium compounds, various sulfonium compounds, various trihalomethyltriazine compounds, and the like.

Color Filter

The color filter of the present invention contains at least a compound represented by the above-mentioned Formula (I) as a colorant. In addition, it is preferable that the color filter is manufactured by using the composition of the present invention.

The color filter of the present invention can be manufactured by coating the composition of the present invention on a support by using a coating method, such as a spin coating, a casting coating, or a roll coating, to form a radiation-sensitive composition layer, exposing the resultant to light through a prescribed mask pattern, and developing the resultant with a developing solution to form a colored pattern. Further, the manufacturing method for the color filter of the present invention may include a process for curing the above-mentioned resist pattern by heating and/or exposing to light, in accordance with necessity. Moreover, the process for curing by heating and/or or exposing to light may be carried out a plurality of times.

Preferable examples of the radiation used in this case include ultraviolet radiation such as g-ray, h-ray or i-ay.

Examples of the above-mentioned support include soda glass, PYREX® glass, silica glass, and these to which a transparent electrically conductive film is deposited; a photoelectric transducer substrate such as a silicone substrate, which is used in image pickup elements or the like; a complementary metal oxide semiconductor (CMOS), and the like. Black stripes for optically isolating the respective pixels may be formed on these supports.

Further, in view of improving adherence the substrate to the upper layer, preventing substance diffusion, and/or flattening the substrate surface, an undercoating layer may be provided on the support in accordance with necessity.

Any developing solution can be used as the developing solution involved in the manufacturing method for the above-mentioned color filter of the present invention, provided that it is a composition which dissolves the composition of the present invention, but do not dissolve radiation-irradiated portions. Specific examples thereof include a combination of various organic solvents and alkaline aqueous solutions.

Examples of the above-mentioned organic solvents include the aforementioned solvents which are used in preparing the composition of the present invention.

Examples of the alkaline aqueous solution include an alkaline aqueous solution in which an alkaline compound such as sodium hydroxide, potassium hydroxide, sodium carbonate, sodium silicate, sodium metasilicate, ammonia water, ethylamine, diethylamine, dimethylethanolamine, tetramethylammoniumhydroxide, tetraethylammoniumhydroxide, choline, pyrrole, piperidine or 1,8-diazabicyclo-[5.4.0]-7-undecene is dissolved such that a concentration thereof becomes 0.01 to 10% by mass, preferably 0.01 to 1% by mass. When a developing solution consisting of such an alkaline aqueous solution is used, the color filter is generally cleaned with water after a development.

Further, the color filter of the present invention can be used for solid image pickup elements such as a liquid crystal display device or a CCD, and is particularly suited for use with CCDs and CMOSs which have a high resolution of over one million pixels, and the like. The color filter of the present invention can be used as a color filter to be disposed between the light receiving part of the respective pixels constituting the CCD and condensing microlenses, for example.

EXAMPLES

Hereinafter, the present invention will be more specifically described with examples. However, the present invention is not limited by the following examples, in other words, other forms of the invention may be produced within the spirit or scope of the invention as defined in the appended claims. In the following description, the words "part" and "%" are used based on mass unless otherwise noted.

Example of Synthesis 1

Synthesis of Exemplified Compound (1)

In accordance with the following scheme, synthesis of the compound (colorant) in the present invention was conducted.

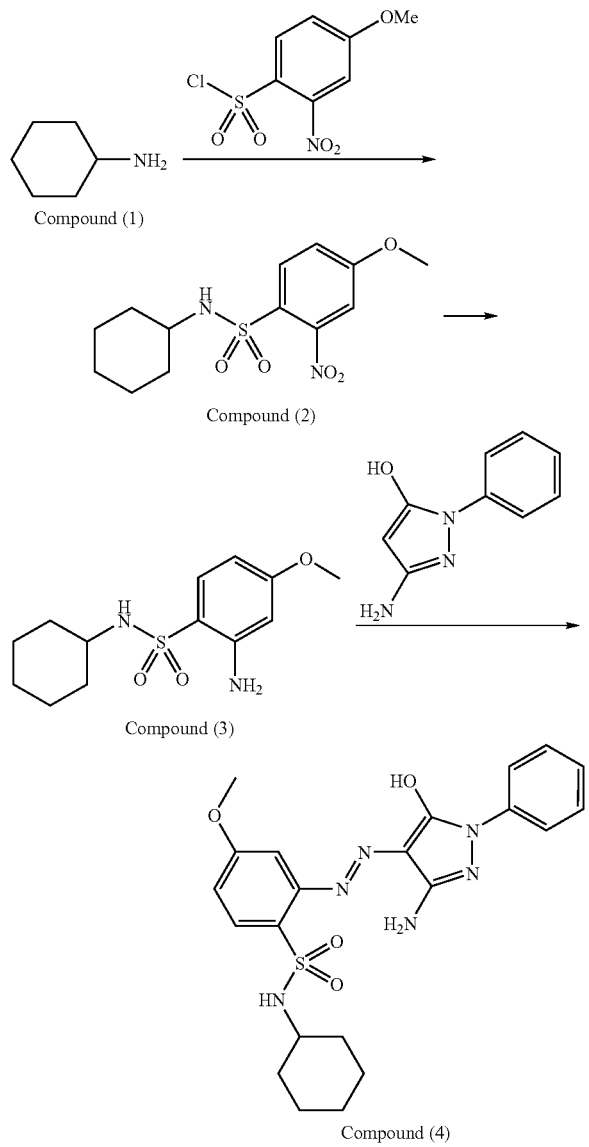

11.28 g of cyclohexylamine [the above-mentioned compound (1)], 27 g of 4-methoxy-2-nitrobenzenesulfonylchloride, 54 ml of orthodichlorobenzen, and 4.3 ml of distilled water were mixed, and stirred for 1 hr at room temperature. After being stirred, the mixture was heated to 50° C., which was followed by adding an aqueous solution of 5.69 g of sodium carbonate to the mixture, and further stirring it for 1 hr at a temperature of 70° C. Then, the reaction mixture was poured into water, and extracted with ethyl acetate, and the ethyl acetate phase was washed with 4% sulfuric acid in water. Thereinafter, magnesium sulfate and activated carbon were added to the ethyl acetate phase for drying and decoloring it, and the dried and decolored ethyl acetate phase was subjected to the celite filtration. This ethyl acetate phase was concentrated to obtain the above-mentioned compound (2).

Then, 35 g of reduced iron, 25 g of acetic acid, and 75 g of water were mixed, and stirred at 80° C., and to the mixture, the compound (2) obtained in the above-mentioned manner was gradually added, then the mixture was stirred for 2 hr at 80° C. Then, 26 ml of ethanol was added to the reaction mixture, which was then refluxed and stirred for 2.5 hr. After being stirred, the reaction mixture was cooled to room temperature, and after 32.5 g of sodium carbonate being added thereto, 200 ml of acetic acid, and celite and activated carbon were further added for celite filtration. Then, the organic layer was steam-distilled to obtain 24.78 g of the above-mentioned compound (3) (the overall yield was 80%).

Then, 5.69 g of the above-mentioned compound (3), 0.09 g of tetraethylammoniumchloride, 100 ml of acetic acid, 7.3 ml of 36% hydrochloric acid, and 11 ml of distilled water were mixed, and cooled to 0° C. To the mixture, an aqueous solution of sodium nitrite ($NaNO_2$: 1.4 g; and water: 10 g) was added dropwise with the internal temperature being kept at 5° C. or lower, and after the drip addition, the mixture was stirred for 3 hr with the temperature being maintained at 5 to 10° C. to obtain a diazo solution.

The diazo solution was added dropwise into a separately prepared slurry solution of 3-amino-1-phenyl-2-pyrazoline-5-one (3.71 g of 3-amino-1-phenyl-2-pyrazoline-5-one, 40 g of water, and 2.14 g of 36% hydrochloric acid) over a time period of 30 min at 0° C. or below. Then, 38 ml of a 40% aqueous solution of sodium acetate was dropped into the slurry solution over a time period of 1 hr, which was then followed by adding dropwise 50 ml of 10% aqueous sodium carbonate, and stirring over night. Then, 100 ml of a 50% aqueous solution of sodium hydroxide was added dropwise into the mixture, which was heated to 65° C., and stirred for 1 hr before being cooled to room temperature. The obtained mixture was filtered, and washed with an alkaline saline solution to obtain 6.80 g of the above-mentioned exemplified compound (1), which is the compound (dye) as the object of the present invention (the yield was 75%).

The exemplified compound (1) obtained in the above-mentioned way was analyzed by NMR for structure verification with the following data being given. $^1$H-NMR (300 MHz; solvent: dimethyl-$d_6$sulfoxyde; standard substance: tetramethylsilane) δ 7.95 ppm (2H, d), 7.80 (2H, m), 7.62 (1H, s), 7.43 (2H, t), 7.15 (1H, t), 6.85 (1H, d), 6.65 (2H, s), 3.95 (3H, s), 3.10 (1H, m), 1.60 (4H, m), 1.43 (1H, m), 1.25 to 0.85 (6H, m).

Further, the above-mentioned exemplified compound (1) was dissolved into methanol to prepare a solution having a concentration of approx. $1.0 \times 10^{-5}$ mol/l, and by using a spectrophotometer (trade name: UV-2500PC, manufactured by Shimadzu Corporation), measurement of the maximal absorption wavelength ($\lambda$max) and molar absorption coefficient ($\epsilon$), as well as measurement of the peak width at half height from the wavelength were carried out. As a result of this, it was found that, in methanol, $\lambda$max=384 nm, and $\epsilon$=25800 (1*mol$^{-1}$ cm$^{-1}$) (peak width at half height=70.5 nm).

Example 1

1) Preparation of Resist Solution

The following compositions were mixed and dissolved to prepare a resist solution.

Compositions for Resist Solution

| | |
|---|---|
| Propyleneglycolmonomethyl ether acetate (PGMEA) | 19.00 parts |
| Ethyl lactate | 36.00 parts |
| Cyclohexanone | 0.87 parts |
| Binder (PGMEA solution containing 41% of acrylmethacrilate/methacrylic acid copolymer (molar ratio = 65:35)) | 30.51 parts |
| Dipentaerythritolhexacrilate | 12.20 parts |
| Polymerization inhibitor (p-methoxyphenol) | 0.0075 parts |
| Fluorine surfactant (trade name: MEGAFACE ® F177P, 0.2% ethyl lactate solution, manufactured by Dainippon Ink And Chemicals, Inc.) | 0.95 parts |
| 2-(O-benzoyloxime)-1-[4-(phenylthio)phenyl]-1,2-octanedion (photopolymerization initiator) | 0.600 parts |

2) Preparation of Glass Substrate Having Undercoating Layer

A glass substrate (trade name: CORNING 1737, manufactured by Corning Inc.) was ultrasonically washed with 1% NaOH water, which was then followed by water washing and dehydration baking (for 30 min at 200° C.).

Next, the above-mentioned resist solution was applied to the washed glass substrate to provide a film thickness of 2 μg m by means of a spin coater, and heated to be dried for 1 hr at 220° C. for formation of a cured film to obtain a glass substrate having an undercoating layer.

3) Preparation of Colorant-Containing Resist Solution 9.4 g of the resist solution obtained in the above paragraph 1) and 0.6 g of the above-mentioned exemplified compound (1) [colorant: a compound represented by the Formula (I)] were mixed and dissolved to obtain the colorant-containing resist solution.

4) Light Exposure and Development Processing of Colorant-Containing Resist

Image Formation

The dye resist solution obtained in the above paragraph 3) was applied to the undercoating layer of the glass substrate having an undercoating layer obtained in the above paragraph 2) to provide a film thickness of 1.0 μm by using a spin coater, and prebaked for 120 sec at 120° C.

Next, by using an exposing apparatus, the coated film was irradiated at an amount of exposure of 800 mJ/cm$^2$ with a wavelength of 365 nm through a mask having a thickness of 20 μm. After the exposure, the coated film was processed for development under the conditions of 26° C. and 60 sec by using a developing solution (trade name: CD-2000; concentration: 60%, manufactured by FUJIFILM Arch Co., Ltd.) Thereinafter, the coated film was rinsed for 20 sec with running water, which was then followed by spray drying for image formation.

In the present example, the image formation was verified in the normal way by using an optical microscope and SEM photographic observation.

Further, the "developability of the unexposed parts" and the "percentage of film remaining in the exposed parts" were measured with a chromoscope (trade name: MCPD-1000, manufactured by Otsuka Electronics Co., Ltd.).

The "developability of the unexposed parts" refers to the rate of change in absorbance for the film before and after the development, and for a light sensitive negative composition, the greater the value, the better. Further, the "percentage of film remaining in the exposed part" refers to the ratio of maintained light absorbance for the film before and after development, and for a light sensitive negative composition, the greater the value, the better.

That the above-mentioned developability of the unexposed part and the above-mentioned percentage of film remaining in the exposed part are both high values means that pattern formability is good.

In the present example, the "heat resistance" was determined by heating the glass substrate coated with a dye resist solution for 1 hr at 200° C. by use of a hot plate, and then measuring the change in chromaticity, i.e., the Δ Eab value, with a chromoscope (trade name: MCPD-1000, manufactured by Otsuka Electronics Co., Ltd.). The smaller the Δ Eab value, the higher the heat resistance.

The "light resistance" was determined by irradiating the glass substrate coated with a dye resist solution with a Xenon lamp at 200,000 lux for 10 hr (equivalent to 2,000,000 lux hours), and then measuring the change in chromaticity, i.e., the Δ Eab value. The smaller the Δ Eab value, the higher the light resistance.

The molar absorbance coefficient ($\epsilon$) was calculated from the absorbance in methanol. As the color value, the value obtained by dividing the molar absorbance coefficient ($\epsilon$) by the Mw of the dye, i.e., $\epsilon$/Mw was used.

Table 1 gives the results of these.

Examples 2 to 7

The image was formed in the same way as in Example 1, and the evaluation was carried out in the same manner except that, in the preparation of the colorant-containing resist solution as described in 3) in Example 1, the colorant was substituted by the compounds as shown in Table 1 below. The results are given in Table 1 below.

Examples 8 to 14

Except that the glass substrate in Examples 1 to 7 was substituted by a silicone wafer substrate, the image was formed in the same way as in Example 1. For the developability of the unexposed part and the film remaining percentage for the exposed part, the same results as in Examples 1 to 7 were obtained.

Examples 8 to 14 use a silicone wafer substrate, and thus they are different from Examples 1 to 7 in the substrate used, but since the colorant resist solution is coated on the undercoating layer throughout Examples 1 to 14, thus there arises no substantial difference, resulting in the same performances having been obtained.

Example 15

The image was formed in the same way as in Example 1, and the evaluation was carried out in the same manner except that, in the preparation of the resist solution as described in 1) in Example 1, the photopolymerization initiator was substituted by TAZ-107 (trade name, manufactured by Midori Kagaku Co., Ltd.). The results are given in Table 1 below.

Example 16

The image was formed in the same way as in Example 1, and the evaluation was carried out in the same manner except that, in the preparation of the resist solution as described in 1) in Example 1, the photopolymerization initiator was substituted by 2-benzyl-2-dimethylamino-4-morpholinobutyrophenone, The results are given in Table 1 below.

Comparative Example 1

The image was formed in the same way as in Example 1, and the evaluation was carried out in the same manner except that, in the preparation of the colorant-containing resist solution as described in 3) in Example 1, the colorant was substituted by the following yellow dye (the comparison compounds 1 and 2). The results are given in Table 1 below.

TABLE 1

| | Colorant | Unexposed parts developability | Exposed parts percentage remaining film | Heat resistance δ Eab (200° C./1 h) | Light resistance δ Eab (2 M Lux. 1 h) | Molar absorbance coefficient ε ($1 \cdot mol^{-1} cm^{-1}$) | Color value ε/Mw |
|---|---|---|---|---|---|---|---|
| EXAMPLE 1 | Exemplified compound (1) | 100 | 100 | 2.13 | 2.12 | 25800 | 55 |
| EXAMPLE 2 | Exemplified compound (2) | 100 | 100 | 2.05 | 2.23 | 24200 | 55 |
| EXAMPLE 3 | Exemplified compound (5) | 100 | 100 | 2.55 | 2.34 | 24000 | 52 |
| EXAMPLE 4 | Mixture of exemplified compound (1) and exemplified compound (2) in ratio of 1:1 (mass) | 99 | 100 | 3.26 | 3.28 | — | — |
| EXAMPLE 5 | Mixture of CI Solvent Blue 67, exemplified compound (1), and CI Solvent Yellow 162 in ratio of 0.7:1.0:1.0 (mass) | 99 | 99 | 3.65 | 3.35 | — | — |
| EXAMPLE 6 | Mixture of CI Solvent Blue 25, exemplified compound (2), and CI Solvent Yellow 162 in ratio of 2.0:1.0:1.0 (mass) | 98 | 100 | 3.87 | 3.65 | — | — |
| EXAMPLE 7 | Mixture of CI Solvent Blue 25, exemplified compound (5), CI Solvent Yellow 82, and CI Acid Green 16 in ratio of 3.0:2.0:2.0:1.0 (mass) | 97 | 98 | 3.92 | 3.55 | — | — |
| EXAMPLE 15 | Exemplified compound (1) | 99 | 99 | 3.26 | 3.31 | 25800 | 55 |
| EXAMPLE 16 | Exemplified compound (1) | 98 | 97 | 3.35 | 3.43 | 25800 | 55 |
| COMPARATIVE EXAMPLE | Acid yellow 42 ditolylguanidine salt: dyestuff/ditolylguanidine = 1/2 (molar ratio) | 45 | 89 | 43.50 | 38.50 | 55300 | 46.3 |
| EXAMPLE 17 | Exemplified compound (1) | 0 | 0 | 3.68 | 3.75 | 25800 | 55 |
| EXAMPLE 18 | Exemplified compound (1) | 0 | 0 | 3.78 | 3.68 | 25800 | 55 |

Comparative yellow dye 1: Acid Yellow 42
(Mw = 714.3)

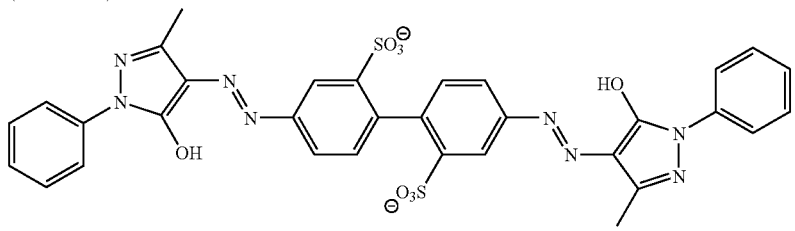

Comparative yellow dye 2: ditolylguanidine
(Mw: 239.32)

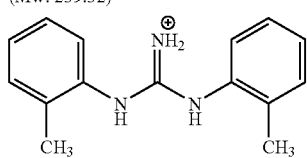

(Mixing ratio of the Acid Yellow 42 ditolylguanidine salt: dye/ditolylguanidine = 1/2 (molar ratio))

As can be seen from Table 1, with the conventionally-known curable compositions, such as the comparative example, it has been difficult to simultaneously meet the requirements for the various performances as given in Table 1. However, by using the colorant-containing curable composition containing a compound represented by the Formula (I) in the present invention, a curable composition which provides excellent performance in heat resistance, light resistance and color value (ε/Mw) of the colorant could be obtained. At the same time, the developability of the unexposed parts and the percentage of film remaining in the exposed parts could be improved, and it has been found that the curable composition obtained is excellent in pattern formability.

Especially with the color value having been improved, the amount of addition of the dye can be reduced, and the various properties, such as the pattern formability, can be improved.

As is obvious from the results as given in Table 1, Comparative Example 1, is that use of a conventional pyrazolone-azo dye offers substantially inferior performances in developability of unexposed parts, precentage of remaining film in exposed parts, heat resistance and light resistance, and the superiority of the aminopyrazolone-azo dye of the present invention has been demonstrated.

Example 17

In the preparation of the colorant-containing resist solution as described in 3) in Example 1, a colored positive photosensitive resin composition A prepared by the following manner was used in place of the colorant-containing resist solution to form an image in the same way as in Example 1 except that full-spectrum light exposure was carried out, and the evaluation was carried out in the same manner as in Example 1. The Results are also Given in Table 1 Below.

Preparation of Colored Positive Photosensitive Resin Composition A

The following compositions were mixed and dissolved to prepare a colored positive photosensitive resin composition.

| | |
|---|---|
| Ethyl lactate | 75.0 parts |
| Binder (P-1) (shown below) | 14.0 parts |
| Exemplified compound (1) (a compound represented by the above-mentioned Formula (I)) | 6.0 parts |
| Photoacid generator (following "PAG-1") | 4.0 parts |
| Fluorine surfactant (trade name: F475, manufactured by Dainippon Ink And Chemicals, Inc.) | 0.4 parts |

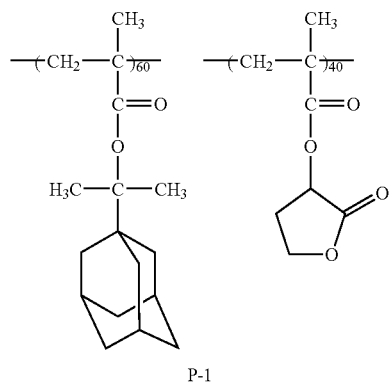

P-1

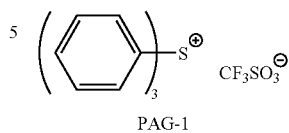

PAG-1

Example 18

In the preparation of the colorant-containing resist solution as described in 3) in Example 1, a colored positive photosensitive resin composition B prepared in the following manner was used in place of the colorant-containing resist solution to form an image in the same way as in Example 1 except that the full-spectrum light exposure was carried out, and the evaluation was carried out in the same manner as in Example 1. The Results are also Given in Table 1 Below.

Preparation of Colored Positive Photosensitive Resin Composition B

| | |
|---|---|
| Ethyl lactate | 210.0 parts |
| A novolak resin which is obtained by condensing p-crezol and formaldehyde (molecular weight in converting to polystyrene: 5500) | 20.0 parts |
| Hexamethoxymethylolmeramine | 15.0 parts |
| Exemplified compound (1) (a compound represented by the above-mentioned Formula (I)) | 35.0 parts |
| Esterized compound of 2,3,4-trihydroxybenzophenone and o-naphthoquinonediazide-5-sulfonylchloride (esterization ratio: 80 mol %; quinonazide compound) | 15.0 parts |
| Ester of [4-(7,8-dihydroxy-2,4,4-trimethyl-2-chromanyl)pyrrogallol] and o-naphthoquinonediazide-5-sulfonic acid | 15.0 parts |

Because Examples 17 and 18 provide a positive photosensitive composition, the lower the value of the developability of the unexposed part and the percentage of remaining film in the exposed part, the more preferable.

As can be seen from Table 1, also in Examples 17 and 18, a positive curable composition which provides excellent performance in heat resistance, light resistance, and color value of the colorant could be obtained.

At the same time, the developability of the unexposed parts and the percentage of film remaining in the exposed parts could be improved, and it has been found that the curable composition obtained is excellent in pattern formability.

What is claimed is:

1. A method for manufacturing a color filter, comprising coating a colorant-containing curable composition on a support, exposing the resultant to light through a mask, and developing the resultant to form a pattern, wherein the colorant-containing curable composition comprises a colorant, and the colorant contains a compound represented by the following Formula (I):

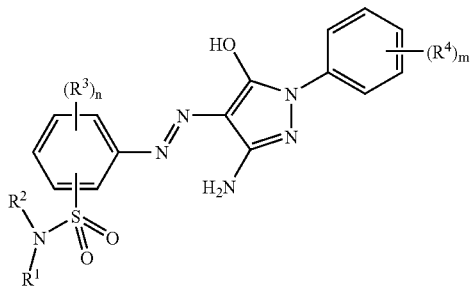

wherein $R^1$ and $R^2$ each independently represent a hydrogen atom, an alkyl group having 1 to 21 carbon atoms, an alkenyl group having 2 to 21 carbon atoms, an aryl group having 6 to 21 carbon atoms, or an aralkyl group having 7 to 21 carbon atoms; $R^1$ and $R^2$ may be formed into a heterocycle together with a jointly bonded nitrogen atom; $R^3$ represents a halogen atom, a trihalomethyl group, an alkoxy group having 1 to 21 carbon atoms, a nitro group, or an amino group; n represents an integer of 0 to 4; $R^4$ represents a halogen atom or a —$SO_3M$ group, in which M represents a hydrogen atom, a cation of a metallic atom, or a cation consisting of a nitrogen-containing compound; and m represents an integer of 0 to 5.

2. The method of claim 1, further comprising curing the pattern by at least method one selected from the group consisting of heating and light exposure.

3. The method of claim 2, wherein the curing by at least one of heating and/or light exposure is carried out a plurality of times.

* * * * *